US009029084B2

(12) United States Patent
Whitcombe et al.

(10) Patent No.: US 9,029,084 B2
(45) Date of Patent: May 12, 2015

(54) POLYNUCLEOTIDE PRIMERS

(75) Inventors: David Mark Whitcombe, Manchester (GB); Nicola Jo Thelwell, Manchester (GB); Paul Francis Ravetto, Manchester (GB)

(73) Assignee: Qiagen Manchester Limited, Manchester (GB)

( * ) Notice: Subject to any disclaimer, the term of this patent is extended or adjusted under 35 U.S.C. 154(b) by 1111 days.

(21) Appl. No.: 11/910,511

(22) PCT Filed: Apr. 4, 2006

(86) PCT No.: PCT/GB2006/001227
§ 371 (c)(1),
(2), (4) Date: Jun. 2, 2008

(87) PCT Pub. No.: WO2006/106316
PCT Pub. Date: Oct. 12, 2006

(65) Prior Publication Data
US 2008/0261219 A1 Oct. 23, 2008

(30) Foreign Application Priority Data

Apr. 4, 2005 (GB) .................................. 0506807.7

(51) Int. Cl.
*C12Q 1/68* (2006.01)
(52) U.S. Cl.
CPC ............ *C12Q 1/6886* (2013.01); *C12Q 1/6851* (2013.01); *C12Q 1/6883* (2013.01); *C12Q 2600/16* (2013.01)
(58) Field of Classification Search
None
See application file for complete search history.

(56) References Cited

U.S. PATENT DOCUMENTS

| | | | |
|---|---|---|---|
| 5,474,796 A * | 12/1995 | Brennan | 427/2.13 |
| 5,830,713 A | 11/1998 | Ferrari et al. | |
| 5,993,813 A | 11/1999 | Mezes et al. | |
| 6,037,130 A * | 3/2000 | Tyagi et al. | 435/6.11 |
| 6,365,355 B1 | 4/2002 | McCutchen-Maloney | |
| 6,444,465 B1 | 9/2002 | Wyatt et al. | |
| 6,528,640 B1 | 3/2003 | Beigelman et al. | |
| 6,582,908 B2 * | 6/2003 | Fodor et al. | 506/9 |
| 6,617,438 B1 | 9/2003 | Beigelman et al. | |
| 6,623,962 B1 | 9/2003 | Akhtar et al. | |
| 2001/0053519 A1 * | 12/2001 | Fodor et al. | 435/6 |
| 2003/0032090 A1 | 2/2003 | Hardiman et al. | |
| 2003/0138912 A1 | 7/2003 | Busfield et al. | |
| 2004/0115660 A1 | 6/2004 | Stacker et al. | |
| 2004/0115712 A1 | 6/2004 | Engel et al. | |
| 2004/0265845 A1 * | 12/2004 | Hoon et al. | 435/6 |

FOREIGN PATENT DOCUMENTS

| | | | |
|---|---|---|---|
| EP | 0 332 495 A2 | 9/1989 | |
| EP | 0332435 A2 | 9/1989 | |
| EP | 0706799 B1 | 4/1996 | |
| EP | 1288314 A2 * | 3/2003 | |
| WO | 9103489 A1 | 3/1991 | |
| WO | 9404689 A1 | 3/1994 | |
| WO | 99/66071 A1 | 12/1999 | |
| WO | 00/61729 A2 | 10/2000 | |
| WO | 0166800 A2 | 9/2001 | |
| WO | 0238599 A2 | 5/2002 | |
| WO | 0242462 A2 | 5/2002 | |
| WO | 02072608 A2 | 9/2002 | |
| WO | 03/057926 A1 | 7/2003 | |
| WO | 03070912 A2 | 8/2003 | |
| WO | 2004011625 A2 | 2/2004 | |
| WO | 20041011625 A2 | 2/2004 | |
| WO | 20041030750 A1 | 4/2004 | |
| WO | 2004042054 A1 | 5/2004 | |
| WO | 20051118876 A2 | 12/2005 | |

OTHER PUBLICATIONS

Genbank Accession No. X00588 (Jul. 6, 1989).*
Brabender et al. (Clin Cancer Res. Jul. 2001;7(7):1850-5).*
Genbank Accession No. BV204024 (Jun. 4, 2004).*
Stratagene ("Gene Characterization Kits" 1988).*
Gen Bank Accession No. BD065255 (Aug. 27, 2002).*
Gen Bank Accession No. CQ766756 (Mar. 3, 2004).*
Kosaka, Takayuki et al., "Mutations of the Epidermal Growth Factor Receptor Gene in Lung Cancer: Biological and Clinical Implications," Cancer Research, 64(24): 8919-8923 (Dec. 15, 2004).
European Opposition Brief, EP 1866438/06726631.2, Proprietor: QIAGEN Manchester Limited, Opponent: Roche Diagnostics GmbH, Notice of Opposition (dated Oct. 17, 2012) against EP Patent No. 1 866 438 B1, reference No. R68260EPEIN Bö, 26 pages.
Didenko, V.V., "DNA Probes Using Fluorescence Resonance Energy Transfer (FRET): Designs and Applications," Biotechniques, Nov. 2001, vol. 31, No. 5, pp. 1106-1121.
Tsan, A., Experimental Report 1, Exhibit 1, Oct. 15, 2012, 3 pages.
Tsan, A., Experimental Report 2, Exhibit 2, Oct. 15, 2012, 3 pages.
NCBI Reference Sequence: NM_005228.2 (Homo sapiens epidermal growth factor receptor (erythroblastic leukemia viral (v-erb-b) oncogene homolog, avian) (EGFR), mRNA, status: Dec. 22, 2003 (obtainable via http://www.ncbi.nlm.nih.gov/nuccore/29725608), 28 pages.
Kosaka, T. et al., "Mutation of the Epidermal Growth Factor Receptor Gene in Lung Cancer: Biological and Clinical Implications," Cancer Research, Dec. 15, 2004, vol. 64, No. 24, pp. 8919-8923.
Lynch, T.J. et al., "Activating Mutations in the Epidermal Growth Factor Receptor Underlying Responsiveness of Non-Small-Cell Lung Cancer to Gefitinib," The New England Journal of Medicine, May 20, 2004, vol. 350, No. 21, pp. 2129-2139.

(Continued)

*Primary Examiner* — Christopher M Babic
*Assistant Examiner* — Aaron Priest
(74) *Attorney, Agent, or Firm* — Rothwell, Figg, Ernst & Manbeck P.C.

(57) ABSTRACT

A polynucleotide primer comprising at least the final six nucleotides of one of the following primer sequences, or a sequence complementary thereto: SEQ. ID NOS. 1 to 18, 21 to 45 or 74 to 77.

20 Claims, 7 Drawing Sheets

(56) References Cited

OTHER PUBLICATIONS

Newton, C.R. et al., "Analysis of Any Point Mutation in DNA, the Amplification Refractory Mutation System (ARMS)," Nucleic Acids Research, Apr. 11, 1989, vol. 17, No. 7, pp. 2503-2516.

Punia, P. et al., "Chapter 9: The Quantitative Amplification Refractory Mutation System," in Real-Time PCR: An Essential Guide, Horizon Bioscience, edited by K. Edwards et al., May 2004, 21 pages.

Groden, J. et al., "Mutational Analysis of Patients with Adenomatous Polyposis: Identical Inactivating Mutations in Unrelated Individuals," American Journal of Human Genetics, vol. 52, pp. 263-272, 1993.

Bruscia, E. et al., "Isolation of CF Cell Lines Corrected at ΔF508-CFTR Locus by SFHR-Mediated Targeting," Gene Therapy, 2002, vol. 9, pp. 683-685, copyright 2002 Nature Publishing Group.

Kwok, S. et al., "Design and Use of Mismatched and Degenerate Primers," in PCR Primer—A Laboratory Manual, Cold Spring Harbor Laboratory Press, edited by Dieffenbach and Dveksler, pp. 143-146, 1995.

Paez, J.G. et al., "EGFR Mutations in Lung Cancer: Correlation with Clinical Response to Gefitinib Therapy," Science, Jun. 4, 2004, vol. 304, pp. 1497-1500.

* cited by examiner

SEQUENCE LISTING

```
<160> NUMBER OF SEQ ID NOS: 77

<210> SEQ ID NO 1
<211> LENGTH: 20
<212> TYPE: DNA
<213> ORGANISM: Homo sapiens

<400> SEQUENCE: 1
cccgtcgcta tcaaggacca                                          20

<210> SEQ ID NO 2
<211> LENGTH: 25
<212> TYPE: DNA
<213> ORGANISM: Homo sapiens

<400> SEQUENCE: 2
ttaaaattcc cgtcgctatc aaaac                                    25

<210> SEQ ID NO 3
<211> LENGTH: 25
<212> TYPE: DNA
<213> ORGANISM: Homo sapiens

<400> SEQUENCE: 3
ttaaaattcc cgtcgctatc aaaac                                    25

<210> SEQ ID NO 4
<211> LENGTH: 21
<212> TYPE: DNA
<213> ORGANISM: Homo sapiens

<400> SEQUENCE: 4
ccgtcgctat caaggaatcg a                                        21

<210> SEQ ID NO 5
<211> LENGTH: 27
<212> TYPE: DNA
<213> ORGANISM: Homo sapiens

<400> SEQUENCE: 5
caaggaatta agagaagcaa cactcga                                  27

<210> SEQ ID NO 6
<211> LENGTH: 26
<212> TYPE: DNA
<213> ORGANISM: Homo sapiens

<400> SEQUENCE: 6
catgtcaaga tcacagattt tgggag                                   26
```

```
<210> SEQ ID NO 7
<211> LENGTH: 20
<212> TYPE: DNA
<213> ORGANISM: Homo sapiens

<400> SEQUENCE: 7
tttctcttcc gcacccagat                                                    20

<210> SEQ ID NO 8
<211> LENGTH: 27
<212> TYPE: DNA
<213> ORGANISM: Homo sapiens

<400> SEQUENCE: 8
ctgaattcaa aaagatcaaa gtgccgt                                            27

<210> SEQ ID NO 9
<211> LENGTH: 27
<212> TYPE: DNA
<213> ORGANISM: Homo sapiens

<400> SEQUENCE: 9
ctgaattcaa aaagatcaaa gtgccga                                            27

<210> SEQ ID NO 10
<211> LENGTH: 27
<212> TYPE: DNA
<213> ORGANISM: Homo sapiens

<400> SEQUENCE: 10
cgtcgctatc aaggaattaa gagaagc                                            27

<210> SEQ ID NO 11
<211> LENGTH: 21
<212> TYPE: DNA
<213> ORGANISM: Homo sapiens

<400> SEQUENCE: 11
gagagcacat ctccgaaagc c                                                  21

<210> SEQ ID NO 12
<211> LENGTH: 26
<212> TYPE: DNA
<213> ORGANISM: Homo sapiens

<400> SEQUENCE: 12
catgtcaaga tcacagattt tggcct                                             26

<210> SEQ ID NO 13
<211> LENGTH: 20
<212> TYPE: DNA
<213> ORGANISM: Homo sapiens

<400> SEQUENCE: 13
tttctcttcc gcacccacca                                                    20

<210> SEQ ID NO 14
<211> LENGTH: 27
<212> TYPE: DNA
<213> ORGANISM: Homo sapiens

<400> SEQUENCE: 14
```

```
ctgaattcaa aaagatcaaa gtgctcg                                        27

<210> SEQ ID NO 15
<211> LENGTH: 25
<212> TYPE: DNA
<213> ORGANISM: Homo sapiens

<400> SEQUENCE: 15
gagatgagca gggtctagag cagag                                          25

<210> SEQ ID NO 16
<211> LENGTH: 25
<212> TYPE: DNA
<213> ORGANISM: Homo sapiens

<400> SEQUENCE: 16
gctgacctaa agccacctcc ttact                                          25

<210> SEQ ID NO 17
<211> LENGTH: 25
<212> TYPE: DNA
<213> ORGANISM: Homo sapiens

<400> SEQUENCE: 17
ctgtttcagg gcatgaacta cttgg                                          25

<210> SEQ ID NO 18
<211> LENGTH: 25
<212> TYPE: DNA
<213> ORGANISM: Homo sapiens

<400> SEQUENCE: 18
cctttggtct gtgaattggt ctcac                                          25

<210> SEQ ID NO 19
<211> LENGTH: 32
<212> TYPE: DNA
<213> ORGANISM: Artificial Sequence
<220> FEATURE:
<223> OTHER INFORMATION: Scorpions primer tail
<220> FEATURE:
<221> NAME/KEY: misc_feature
<222> LOCATION: (1)..(32)
<223> OTHER INFORMATION: Scorpions primer tail

<400> SEQUENCE: 19
ccgcgggatt tccttgttgg ctttcgccgc gg                                  32

<210> SEQ ID NO 20
<211> LENGTH: 32
<212> TYPE: DNA
<213> ORGANISM: Artificial Sequence
<220> FEATURE:
<223> OTHER INFORMATION: Scorpions primer tail
<220> FEATURE:
<221> NAME/KEY: misc_feature
<222> LOCATION: (1)..(32)
<223> OTHER INFORMATION: Scorpions primer tail

<400> SEQUENCE: 20
ccgcggattc tttctcttcc gcaccccgc gg                                   32

<210> SEQ ID NO 21
<211> LENGTH: 26
<212> TYPE: DNA
<213> ORGANISM: Homo sapiens
```

```
<400> SEQUENCE: 21
ttaaaattcc cgtcgctatc aagaca                                          26

<210> SEQ ID NO 22
<211> LENGTH: 23
<212> TYPE: DNA
<213> ORGANISM: Homo sapiens

<400> SEQUENCE: 22
acctccaccg tgcagctcat cct                                             23

<210> SEQ ID NO 23
<211> LENGTH: 23
<212> TYPE: DNA
<213> ORGANISM: Homo sapiens

<400> SEQUENCE: 23
acctccaccg tgcagctcat aac                                             23

<210> SEQ ID NO 24
<211> LENGTH: 25
<212> TYPE: DNA
<213> ORGANISM: Homo sapiens

<400> SEQUENCE: 24
atggcaaact cttgctatcc cagga                                           25

<210> SEQ ID NO 25
<211> LENGTH: 22
<212> TYPE: DNA
<213> ORGANISM: Homo sapiens

<400> SEQUENCE: 25
cttgttggct ttcggagatg gt                                              22

<210> SEQ ID NO 26
<211> LENGTH: 24
<212> TYPE: DNA
<213> ORGANISM: Homo sapiens

<400> SEQUENCE: 26
ttgttggctt tcggagatgt tttg                                            24

<210> SEQ ID NO 27
<211> LENGTH: 23
<212> TYPE: DNA
<213> ORGANISM: Homo sapiens

<400> SEQUENCE: 27
ggatttcctt gttggctttc gat                                             23

<210> SEQ ID NO 28
<211> LENGTH: 24
<212> TYPE: DNA
<213> ORGANISM: Homo sapiens

<400> SEQUENCE: 28
caaagcagaa actcacatcg agtg                                            24

<210> SEQ ID NO 29
<211> LENGTH: 26
<212> TYPE: DNA
```

```
<213> ORGANISM: Homo sapiens

<400> SEQUENCE: 29
ctcttccgca cccagcagtt tggcac                                          26

<210> SEQ ID NO 30
<211> LENGTH: 26
<212> TYPE: DNA
<213> ORGANISM: Homo sapiens

<400> SEQUENCE: 30
atcacagatt ttgggctggc caataa                                          26

<210> SEQ ID NO 31
<211> LENGTH: 28
<212> TYPE: DNA
<213> ORGANISM: Homo sapiens

<400> SEQUENCE: 31
tatacaccgt gccgaacgca ccggaaca                                        28

<210> SEQ ID NO 32
<211> LENGTH: 28
<212> TYPE: DNA
<213> ORGANISM: Homo sapiens

<400> SEQUENCE: 32
tatacaccgt gccgaacgca ccggatct                                        28

<210> SEQ ID NO 33
<211> LENGTH: 22
<212> TYPE: DNA
<213> ORGANISM: Homo sapiens

<400> SEQUENCE: 33
ttgttggctt tcggagatgt ct                                              22

<210> SEQ ID NO 34
<211> LENGTH: 21
<212> TYPE: DNA
<213> ORGANISM: Homo sapiens

<400> SEQUENCE: 34
agccgaaggg catgagctga g                                               21

<210> SEQ ID NO 35
<211> LENGTH: 23
<212> TYPE: DNA
<213> ORGANISM: Homo sapiens

<400> SEQUENCE: 35
ggctttcgga gatgttgctt ctc                                             23

<210> SEQ ID NO 36
<211> LENGTH: 27
<212> TYPE: DNA
<213> ORGANISM: Homo sapiens

<400> SEQUENCE: 36
gcttctctta attccttgat agcgacg                                         27

<210> SEQ ID NO 37
<211> LENGTH: 26
```

<212> TYPE: DNA
<213> ORGANISM: Homo sapiens

<400> SEQUENCE: 37
ctcttccgca cccagcagtt tggtca                                  26

<210> SEQ ID NO 38
<211> LENGTH: 26
<212> TYPE: DNA
<213> ORGANISM: Homo sapiens

<400> SEQUENCE: 38
atcacagatt ttgggctggc caatca                                  26

<210> SEQ ID NO 39
<211> LENGTH: 28
<212> TYPE: DNA
<213> ORGANISM: Homo sapiens

<400> SEQUENCE: 39 tataccgt gccgaacgca ccggagac                                  28

<210> SEQ ID NO 40
<211> LENGTH: 21
<212> TYPE: DNA
<213> ORGANISM: Homo sapiens

<400> SEQUENCE: 40
agccgaaggg catgagcttc a                                       21

<210> SEQ ID NO 41
<211> LENGTH: 25
<212> TYPE: DNA
<213> ORGANISM: Homo sapiens

<400> SEQUENCE: 41
ctggtaacat ccacccagat cactg                                   25

<210> SEQ ID NO 42
<211> LENGTH: 28
<212> TYPE: DNA
<213> ORGANISM: Homo sapiens

<400> SEQUENCE: 42
ttcccatgat gatctgtccc tcacagca                                28

<210> SEQ ID NO 43
<211> LENGTH: 28
<212> TYPE: DNA
<213> ORGANISM: Homo sapiens

<400> SEQUENCE: 43
gagctcaccc agaatgtctg gagagcat                                28

<210> SEQ ID NO 44
<211> LENGTH: 28
<212> TYPE: DNA
<213> ORGANISM: Homo sapiens

<400> SEQUENCE: 44
gggctgaggt gacccttgtc tctgtgtt                                28

<210> SEQ ID NO 45

```
<211> LENGTH: 25
<212> TYPE: DNA
<213> ORGANISM: Homo sapiens

<400> SEQUENCE: 45
gcacagcttt tcctccatga gtacg                                          25

<210> SEQ ID NO 46
<211> LENGTH: 19
<212> TYPE: DNA
<213> ORGANISM: Artificial Sequence
<220> FEATURE:
<223> OTHER INFORMATION: primer

<400> SEQUENCE: 46
accgtgcagc tcatcatgc                                                 19

<210> SEQ ID NO 47
<211> LENGTH: 100
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(100)
<223> OTHER INFORMATION: Primer

<400> SEQUENCE: 47
aaaattcccg tcgctatcaa acatctccg aaagccaaca aggaaatcct cgatgtgagt     60
ttctgctttg ctgtgtgggg gtccatggct ctgaacctca                         100

<210> SEQ ID NO 48
<211> LENGTH: 90
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(90)
<223> OTHER INFORMATION: Primer

<400> SEQUENCE: 48
aacatttagg atgtggagat gagcagggtc tagagcagag cagctgccag acatgagaaa    60
aggtgggcct gaggttcaga gccatggacc                                    90

<210> SEQ ID NO 49
<211> LENGTH: 100
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(100)
<223> OTHER INFORMATION: Primer

<400> SEQUENCE: 49
cgctatcaag gaatcgaaag ccaacaagga atcctcgat gtgagtttct gctttgctgt     60
gtgggggtcc atggctctga acctcaggcc cacctttct                          100

<210> SEQ ID NO 50
<211> LENGTH: 93
<212> TYPE: DNA
<213> ORGANISM: Artificial Sequence
```

```
<220> FEATURE:
<223> OTHER INFORMATION: Primer
<220> FEATURE:
<221> NAME/KEY: misc_feature
<222> LOCATION: (1)..(93)
<223> OTHER INFORMATION: Primer

<400> SEQUENCE: 50
agaaagacat agaaagtgaa catttaggat gtggagatga gcagggtcta gagcagagca    60
gctgccagac atgagaaaag gtgggcctga ggt                                 93

<210> SEQ ID NO 51
<211> LENGTH: 100
<212> TYPE: DNA
<213> ORGANISM: Artificial Sequence
<220> FEATURE:
<223> OTHER INFORMATION: Primer

<400> SEQUENCE: 51
gctatcaagg aattaagaga agcaacactc gatgtgagtt tctgctttgc tgtgtggggg    60
tccatggctc tgaacctcag gcccaccttt tctcatgtct                         100

<210> SEQ ID NO 52
<211> LENGTH: 86
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(86)
<223> OTHER INFORMATION: Primer

<400> SEQUENCE: 52
agaaagacat agaaagtgaa catttaggat gtggagatga gcagggtcta gagcagagca    60
gctgccagac atgagaaaag gtgggc                                         86

<210> SEQ ID NO 53
<211> LENGTH: 100
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(100)
<223> OTHER INFORMATION: Primer

<400> SEQUENCE: 53
aattcccgtc gctatcaagg aaccatctcc gaaagccaac aaggaaatcc tcgatgtgag    60
tttctgcttt gctgtgtggg ggtccatggc tctgaacctc                         100

<210> SEQ ID NO 54
<211> LENGTH: 93
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(93)
<223> OTHER INFORMATION: Primer

<400> SEQUENCE: 54
gtgaacattt aggatgtgga gatgagcagg gtctagagca gagcagctgc cagacatgag    60
```
aaaaggtggg cctgaggttc agagccatgg acc                          93

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55
cgccatgcac aacttcccta c                                       21

<210> SEQ ID NO 56
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Primer

<400> SEQUENCE: 56
tccagaattt aatgatgctg cgtct                                   25

<210> SEQ ID NO 57
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(17)
<223> OTHER INFORMATION: Primer

<400> SEQUENCE: 57
gaacgcaccg gagcaca                                            17

<210> SEQ ID NO 58
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Primer

<400> SEQUENCE: 58
ttggtgacat gttggtacat ccatc                                   25

<210> SEQ ID NO 59
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: Primer

<400> SEQUENCE: 59
ttcaaaaaga tcaaagtgct gtgc                                    24

```
<210> SEQ ID NO 60
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Primer

<400> SEQUENCE: 60
cgttaactgg caattgtgag atggt                                    25

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
agtccagtaa gttcaagccc aggtc                                    25

<210> SEQ ID NO 62
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Primer

<400> SEQUENCE: 62
gttccttagg tgtccttgac agcag                                    25

<210> SEQ ID NO 63
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(17)
<223> OTHER INFORMATION: Primer

<400> SEQUENCE: 63
ccagcagttt ggcccgc                                             17

<210> SEQ ID NO 64
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Primer

<400> SEQUENCE: 64
cagagatttc aattgcagcg agatt                                    25

<210> SEQ ID NO 65
<211> LENGTH: 21
<212> TYPE: DNA
```

```
<213> ORGANISM: Artificial Sequence
<220> FEATURE:
<223> OTHER INFORMATION: Primer
<220> FEATURE:
<221> NAME/KEY: misc_feature
<222> LOCATION: (1)..(21)
<223> OTHER INFORMATION: Primer

<400> SEQUENCE: 65
agatcacaga ttttgggcgg g                                              21

<210> SEQ ID NO 66
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Primer

<400> SEQUENCE: 66
taggtttctg agcaccctct gtgtc                                          25

<210> SEQ ID NO 67
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: Primer

<400> SEQUENCE: 67
tctcttccgc acccagctgt                                                20

<210> SEQ ID NO 68
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(18)
<223> OTHER INFORMATION: Primer

<400> SEQUENCE: 68
ttgggctggc caaacagc                                                  18

<210> SEQ ID NO 69
<211> LENGTH: 25
<212> TYPE: DNA
<213> ORGANISM: Artificial Sequence
<220> FEATURE:
<223> OTHER INFORMATION: Primer

<400> SEQUENCE: 69
gctgtgaaat acctggcttg ttgtt                                          25

<210> SEQ ID NO 70
<211> LENGTH: 19
<212> TYPE: DNA
<213> ORGANISM: Artificial Sequence
<220> FEATURE:
<223> OTHER INFORMATION: Primer
```

```
<400> SEQUENCE: 70
gaagggcatg agctgcatg                                               19

<210> SEQ ID NO 71
<211> LENGTH: 25
<212> TYPE: DNA
<213> ORGANISM: Artificial Sequence
<220> FEATURE:
<223> OTHER INFORMATION: Primer

<400> SEQUENCE: 71
ccaggcagcc tttagtcact gtaga                                        25

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
ggcctctctg tcatggggaa t                                            21

<210> SEQ ID NO 73
<211> LENGTH: 25
<212> TYPE: DNA
<213> ORGANISM: Artificial Sequence
<220> FEATURE:
<223> OTHER INFORMATION: Primer

<400> SEQUENCE: 73
acctgctcca ctccaccact atcac                                        25

<210> SEQ ID NO 74
<211> LENGTH: 20
<212> TYPE: DNA
<213> ORGANISM: Homo sapiens

<400> SEQUENCE: 74
tccaccgtgc agctcatctc                                              20

<210> SEQ ID NO 75
<211> LENGTH: 20
<212> TYPE: DNA
<213> ORGANISM: Homo sapiens

<400> SEQUENCE: 75
tccaccgtgc agctcatctt                                              20

<210> SEQ ID NO 76
<211> LENGTH: 22
<212> TYPE: DNA
<213> ORGANISM: Homo sapiens

<400> SEQUENCE: 76
ttgtctttgt gttcccggac at                                           22

<210> SEQ ID NO 77
<211> LENGTH: 28
<212> TYPE: DNA
<213> ORGANISM: Artificial Sequence
<220> FEATURE:
<223> OTHER INFORMATION: Primer
```

```
<400> SEQUENCE: 77
ccgcggctca tgcccttcgg ctccgcgg                                              28
```

POLYNUCLEOTIDE PRIMERS

This application is a 371 filing of PCT/GB2006/001227, filed Apr. 4, 2006, which claims priority from GB 0506807.7, filed Apr. 4, 2005. These prior applications are incorporated herein by reference.

TECHNICAL FIELD

The present invention relates to a polynucleotide, a kit comprising a polynucleotide and a method for detecting the presence or absence of mutations in a gene.

BACKGROUND ART

Epidermal Growth Factor (EGF) and its corresponding receptor (EGFR) are responsible for modulating growth of many classes of cells. Mutations of EGFR have been implicated in uncontrolled cell proliferation and tumour growth.

Although there are many examples of nucleic acid changes having potential as tumour markers, their value as clinical tools in cancer diagnosis, staging or even screening, needs to be demonstrated and two important criteria must be met. Firstly, nucleic acids of adequate yield and quality must be extracted from the clinical material; secondly, robust and accurate methods of analysis are required. For reliable tumour genotyping to be useful in disease staging any test has to be adequately validated and there should be demonstrable benefits over current methods.

A number of studies have examined the association of lung cancer and its response to gefinitib (AstraZeneca's IRESSA) with mutations in the oncogene, EGFR. However, there have been differences in the spectrum and reported frequencies of EGFR mutations. One major issue is that in order to identify a wide range of possible mutations, nucleotide sequencing of the kinase domain of the EGFR gene has been undertaken in excised tumours. The utility of this approach is limited by a number of factors, mainly:
 1. Not all of the biopsy sample is tumour
 2. Not all tumour carries the mutation For example, as little as 10% of a specimen may be tumour, the remainder being marginal non-tumour cells. Tumours are notoriously heterogeneous in their genetic makeup and as little as 10% of the tumour cells may contain any particular genetic change. In total therefore as little as 1% of a tumour sample for genetic analysis may contain the specific variation of interest.

The detection limits for sequencing are of the order of 15-25%; that is sequencing can detect the rarer allele at levels no worse than 1 in 4 to 1 in 6. As discussed above, the prevalence of the mutation in a given tumour sample may be significantly below such levels. Current approaches require that a degree of sample enrichment be performed, namely an attempt to excise selectively the tumour material from a paraffin-embedded tissue section. This is expensive, time consuming and lacks sensitivity.

In the present invention we have now devised novel diagnostic methods for the detection of EGFR mutations based on the amplification refractory mutation system (ARMS) as disclosed in, for example, EP-A-0332435. Validated tests for four EGFR point mutations and four deletions have been developed and the tests have been applied in an investigation of the incidence of the mutations in tumours from patients. The ARMS technology is capable of selectively amplifying specific sequence variants in a background of alternative sequences.

ARMS is a simple and accurate method and has several benefits over other PCR-based mutation detection systems. Specifically, the technique does not require the use of radioisotopes nor the multiple probing of immobilised PCR amplicons nor the cloning of PCR amplicons.

ARMS avoids the need for DNA sequencing of single-strand conformation polymorphism products, a procedure that could be expected to be constrained by sequence under-representation as discussed above. Similarly, under-represented mutant sequences could go undetected using PCR in conjunction with restriction fragment length polymorphism which is limited to low cycle numbers for the PCR to avoid false positive results. Previously generated amplicons therefore have the potential to cause carry-over contamination when PCR is resumed. ARMS can be performed under conditions in which carry-over contamination is avoided, as in the present invention, allowing the use of high PCR cycle numbers and resulting in exceptionally high detection sensitivity.

DISCLOSURE OF THE INVENTION

Thus, in general terms the present invention relates to a diagnostic method for the detection of EGFR mutations in cancer, particularly lung cancer, using the amplification refractory mutation system (ARMS). The invention also relates to mutation specific primers suitable for use in the method and to diagnostic kits containing these primers.

According to one aspect of the present invention, there is provided a polynucleotide comprising at least the final six nucleotides of one of the following primer sequences, or a sequence complementary thereto: SEQ. ID NOS. 1 to 18, 21 to 45 or 74 to 77. The term "the final six nucleotides" means the six nucleotides at the 3' end of the polynucleotide.

Conveniently, the polynucleotide is less than 100 nucleotides long, preferably less than 80 nucleotides long, more preferably less than 60 nucleotides long, more preferably less than 40 nucleotides, more preferably less than 30 nucleotides long.

Preferably, the polynucleotide comprises at least 75% and more preferably 100% of the final 8, 10, 12, 14, 16, 17, 18 or 20 nucleotides, or the entirety of one of the following primer sequences, or a sequence complementary thereto: SEQ. ID NOS. 1 to 18, 21 to 45 or 74 to 77.

Advantageously, the polynucleotide further comprises a quencher group and a fluorophore group. "Fluorophore groups" are those groups which are capable of absorbing light at a first wavelength and in response emitting light at a second wavelength. A "quencher group" is a group which, when in sufficiently close proximity to a fluorophore group, is capable of preventing, or "quenching", the emission of light from the fluorophore group. Typically, a particular type of quencher group will only work with respect to certain types of fluorophore group.

Conveniently, the quencher group and the fluorophore group are separated by a nucleotide tail sequence comprising first and second regions, the nucleotides of the first region being complementary to but in reverse order from the nucleotides of the second region, such that hybridisation of the first region to the second group results in the quencher group to be sufficiently close to the fluorophore group to quench the fluorophore group.

Preferably, the tail sequence further comprises a third region having a sequence complementary to a region of the EGFR gene.

Advantageously, the polynucleotide comprises at least the final six nucleotides of SEQ. ID NO. 3 or 10 and the tail sequence comprise SEQ. ID NO. 19.

Alternatively, the polynucleotide comprises at least the final six nucleotides of SEQ. ID NOS. 6 or 12 and the tail sequence comprises SEQ. ID NO. 20.

Alternatively, the polynucleotide comprises at least the final six nucleotides of SEQ. ID NO: 76 and the tail sequence comprises SEQ. ID NO: 77.

Conveniently, the quencher group comprises black hole quencher 1 (BHQ1) and the fluorophore group comprises FAM.

Alternatively, the quencher group comprises black hole quencher 2 (BHQ2) and the fluorophore comprises Cal Red.

Preferably, a blocking moiety is provided between the primer sequence and the tail sequence to prevent polymerase mediated chain extension of the tail sequence. A preferred blocking moiety is a hexethylene glycol (HEG) monomer.

According to another aspect of the present invention, there is provided a kit comprising at least a pair of polynucleotides, wherein the pair of polynucleotides comprises at least four or five of the final six nucleotides of one of the following pairs of primer sequences, respectively, or sequences complementary thereto: SEQ. ID NO. 1 and SEQ. ID NO. 15, or SEQ. ID NO. 2 and SEQ. ID NO 15, or SEQ. ID NO. 3 and SEQ. ID NO. 15, or SEQ. ID NO. 4 and SEQ. ID NO. 15, or SEQ. ID NO. 5 and SEQ. ID NO. 15, or SEQ. ID NO. 6 and SEQ. ID NO. 16, or SEQ. ID NO. 7 and SEQ. ID NO. 17, or SEQ. ID NO. 8 and SEQ. ID NO. 18, or SEQ. ID NO. 9 and SEQ. ID NO. 18, or SEQ. ID NO. 10 and SEQ. ID NO. 15, or SEQ. ID NO. 11 and SEQ. ID NO. 15 or SEQ. ID NO. 12 and SEQ. ID NO. 16, or SEQ. ID NO. 13 and SEQ. ID NO. 17, or SEQ. ID NO. 14 and SEQ. ID NO. 18 or SEQ. ID NO. 21 and SEQ. ID NO. 15, or SEQ. ID NO. 22 and SEQ. ID NO. 24, or SEQ. ID NO. 23 and SEQ. ID NO. 24, or SEQ. ID NO. 25 and SEQ. ID NO. 41, or SEQ. ID NO. 26 and SEQ. ID NO. 41, or SEQ. ID NO. 27 and SEQ. ID NO. 41, or SEQ. ID NO. 28 and SEQ. ID NO. 41, or SEQ. ID NO. 29 and SEQ. ID NO. 42, or SEQ. ID NO. 30 and SEQ. ID NO. 43, or SEQ. ID NO. 31 and SEQ. ID NO. 44, or SEQ. ID NO. 32 and SEQ. ID NO. 44, or SEQ. ID NO. 33 and SEQ. ID NO. 41, or SEQ. ID NO. 34 and SEQ. ID NO. 45, or SEQ. ID NO. 35 and SEQ. ID NO. 41, or SEQ. ID NO. 36 and SEQ. ID NO. 41, or SEQ. ID NO. 37 and SEQ. ID NO. 42, or SEQ. ID NO. 38 and SEQ. ID NO. 43, or SEQ. ID NO. 39 and SEQ. ID NO. 44, or SEQ. ID NO. 40 and SEQ. ID NO. 45, or SEQ. ID NO. 74 and SEQ. ID NO. 76 or SEQ. ID NO. 75 and SEQ. ID NO. 76. For example, the pair of polynucleotides comprises a first polynucleotide consisting of the final six nucleotides of SEQ ID NO. 1 and a second polynucleotide consisting of the final six nucleotides of SEQ ID NO. 15.

According to a further aspect of the present invention, there is provided a kit comprising at least a set of three polynucleotides wherein the set of three polynucleotides comprises at least four or five of the final six nucleotides of one of the following sets of three primer sequences, respectively, or sequences complementary thereto: SEQ. ID NOS. 1, 10 and 15, or SEQ. ID NOS. 2, 10 and 15, or SEQ. ID NOS. 3, 10 and 15, or SEQ. ID NOS. 4, 11 and 15, or SEQ. ID NOS. 5, 11 and 15, or SEQ. ID NOS. 6, 12 and 16, or SEQ. ID NOS. 7, 13 and 17, or SEQ. ID NOS. 8, 14 and 18, or SEQ. ID NOS. 9, 14 and 18, or SEQ. ID NOS. 21, 10 and 15, or SEQ. ID NOS. 22, 23 and 24, or SEQ. ID NOS. 25, 35 and 41, or SEQ. ID NOS. 26, 35 and 41, or SEQ. ID NOS. 27, 36 and 41, or SEQ. ID NOS. 28, 36 and 41, or SEQ. ID NOS. 29, 32 and 42, or SEQ. ID NOS. 30, 38 and 43, or SEQ. ID NOS. 31, 39 and 44, or SEQ. ID NOS. 32, 39 and 44, or SEQ. ID NOS. 33, 35 and 41, or SEQ. ID NOS. 34, 40 and 45 or SEQ. ID NOS. 74, 75, 76. For example, the set of three polynucleotides comprises a first polynucleotide consisting of the final six nucleotides of SEQ ID NO. 1, a second polynucleotide consisting of the final six nucleotides of SEQ IS NO. 10 and a third polynucleotide consisting of the final six nucleotides of SEQ ID NO. 15.

Conveniently the polynucleotides in the kit are as described above.

Preferably, the kit further comprises nucleotide triphosphates, a polymerisation enzyme and/or a buffer solution.

According to another aspect of the present invention, there is provided the use of a polynucleotide or a kit as described above or a polynucleotide comprising four or five of the final six nucleotides of SEQ. ID NOS. 1 to 18, 21 to 45 or 74 to 77 or sequences complementary thereto for detecting a mutation in a nucleic acid sample containing at least a fragment of the EGFR gene.

Advantageously, the fragment of the EGFR gene in the nucleic acid sample is at least 10 nucleotides long, preferably 20 nucleotides long, more preferably 30 nucleotides long and more preferably 40 nucleotides long.

According to a further aspect of the present invention, there is provided a method of detecting the presence or absence of a mutation in the EGFR gene comprising the steps of:
  a) mixing a nucleic acid sample comprising at least a fragment of the EGFR gene with a polynucleotide complementary to a region of the fragment of the EGFR gene; and
  b) detecting hybridisation of the polynucleotide to the nucleic acid sample wherein hybridisation indicates the presence or absence of a mutation.

Advantageously, the polynucleotide is a polynucleotide as described above and comprises at least for or five of the final six nucleotides of SEQ. ID NOS. 1 to 9, 21, 22, 25 to 34 or 75 or sequences complementary thereto and step b) indicates the presence of a mutation.

Preferably, the polynucleotide is a polynucleotide as described above and comprises at least for or five of the final six nucleotides of SEQ. ID NOS. 10 to 14, 23, 35 to 40 or 74 or sequences complementary thereto; and step b) indicates the absence of a mutation.

Conveniently, the method further comprises the step of prior to step a), amplifying the number of copies of the fragment of the EGFR gene using thermal cycling nucleic acid amplification, preferably PCR.

Preferably step b) comprises carrying out DNA polymerisation using the polynucleotide as a first primer and detecting the extension product of polymerisation.

Advantageously, the method step b) comprises the step of mixing the nucleic acid sample and the polynucleotide with a second primer which corresponds to a region of the fragment of the EGFR sequence downstream of the region to which the polynucleotide is complementary and carrying out PCR on the mixture.

Conveniently, the second primer comprises: SEQ. ID NO. 15 and the polynucleotide comprises at least four or five of the final six nucleotides of SEQ. ID NOS. 1 to 5, 10, 11 or 21; SEQ. ID NO. 16 and the polynucleotide comprises at least the four or five final six nucleotides of SEQ. ID NOS. 6 or 12; SEQ. ID NO. 17 and the polynucleotide comprises at least the four or five final six nucleotides of SEQ. ID NOS. 7 or 13; or SEQ. ID NO. 18 and the polynucleotide comprises at least the four or five final six nucleotides of SEQ. ID NOS. 8, 9 or 14; SEQ. ID NO. 24 and the polynucleotide comprises at least four or five of the final six nucleotides of SEQ. ID NOS: 22 or 23; SEQ. ID NO. 41 and the polynucleotide comprises at least four or five of the final six nucleotides of SEQ. ID NOS. 25 to 28, 33, 35 or 36; SEQ. ID NO. 42 and the polynucleotide comprises at least four or five of the final six nucleotides of SEQ. ID NOS. 29 or 37; SEQ. ID NO. 43 and the polynucleotide comprises at least four or five of the final six nucleotides of SEQ. ID NOS. 30 to 38; SEQ. ID NO. 44 and the polynucleotide comprises at least four or five of the final six nucleotides of SEQ. ID NOS. 31, 32 or 39; or SEQ. ID NO. 45 and the polynucleotide comprises at least four or five of the final six nucleotides of SEQ. ID NOS. 34 or 40; SEQ. ID NO. 76 and the polynucleotide comprises at least four or five of the final six nucleotides of SEQ. ID NO. 74 or 75.

Preferably step a) comprises the step of mixing the nucleic acid sample with a pair of a mutation specific polynucleotide and a wild-type specific polynucleotide, the pair being selected from at least four or five of the final six sequences of: SEQ. ID NO: 1 and SEQ. ID NO: 10; SEQ. ID NO: 2 and SEQ. ID NO: 10; SEQ. ID NO: 3 and SEQ. ID NO: 10; SEQ. ID NO: 4 and SEQ. ID NO: 11; SEQ. ID NO: 5 and SEQ. ID NO: 11; SEQ. ID NO: 6 and SEQ. ID NO: 12; SEQ. ID NO: 7 and SEQ. ID NO: 13; SEQ. ID NO: 8 and SEQ. ID NO: 14; SEQ. ID NO: 9 and SEQ. ID NO: 14; SEQ. ID NO: 21 and SEQ. ID NO: 10; SEQ. ID NO: 22 and SEQ. ID NO: 23; SEQ. ID NO: 25 and SEQ. ID NO: 35; SEQ. ID NO: 26 and SEQ. ID NO: 35; SEQ. ID NO: 27 and SEQ. ID NO: 36; SEQ. ID NO: 28 and SEQ. ID NO: 36; SEQ. ID NO: 29 and SEQ. ID NO: 37; SEQ. ID NO: 30 and SEQ. ID NO: 38; SEQ. ID NO: 31 and SEQ. ID NO: 39; SEQ. ID NO: 32 and SEQ. ID NO: 39; SEQ. ID NO: 33 and SEQ. ID NO: 35; SEQ. ID NO: 34 and SEQ. ID NO: 40; or SEQ. ID NO. 74 and SEQ. ID NO. 75.

Advantageously the nucleic acid sample comprises wild-type sequences and mutated sequences and further comprising step c) wherein the number of amplification cycles required to amplify the wild-type sequences to a predetermined quantity is compared with the number of amplification cycles required to amplify the mutated sequences to the predetermined quantity thereby providing an indication of the ratio of the wild type sequences to mutated sequences in the sample.

Conveniently the nucleic acid sample comprises a portion of tumourous tissue and a portion of non-tumourous tissue and wherein step c) further comprises the step determining the ratio of tumourous tissue to non-tumourous tissue in the sample.

Preferably the method further comprises the step of, prior to step a), enriching the nucleic acid sample to increase the ratio of tumourous tissue to non-tumourous tissue in the sample.

Preferably step b) comprises detecting if amplification of at least a portion of the EGFR gene occurs.

Advantageously the polynucleotide comprises a quencher group and a fluorophore group and step b) comprises exposing the mixture to light of a wavelength to which the fluorophore is responsive in the absence of the quencher group and detecting light at the wavelength emitted by the fluorophore group in the absence of the quencher group.

Where reference is made in the specification to "at least four or five of the final six sequences" of a reference sequence, this means that, of the six nucleotides in the reference sequence, either one or two of the nucleotides may be missing or replaced with a different nucleotide. Of course, in some embodiments, the sequence comprises all six of the nucleotides of the reference sequence.

In preferred embodiments of the present invention, reference to "EGFR" is to the human EGFR gene available as accession number NC_000007 in Homo sapiens chromosome 7, region 55054219 . . . 55242525 as on 30 Mar. 2006. In some other embodiments, reference is to the sequence as on 4 Mar. 2005. Both sequences are incorporated herein by reference. In some embodiments, the EGFR gene is not identical to these sequences but is at least 90% identical to either or both of the sequences.

A reference in this specification is made to a percentage of a polynucleotide compared with a reference polynucleotide, this can be determined by algorithms known in the art.

For example the percentage identity between two sequences can be determined using the BLASTP algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402) using default parameters.

BRIEF DESCRIPTION OF DRAWINGS

In order that the present invention may be more readily understood and so that further features thereof may be appreciated, embodiments of the invention will now be described, by way of example, with reference to the accompanying figures in which.

DETAILED DESCRIPTION

Figure 1:
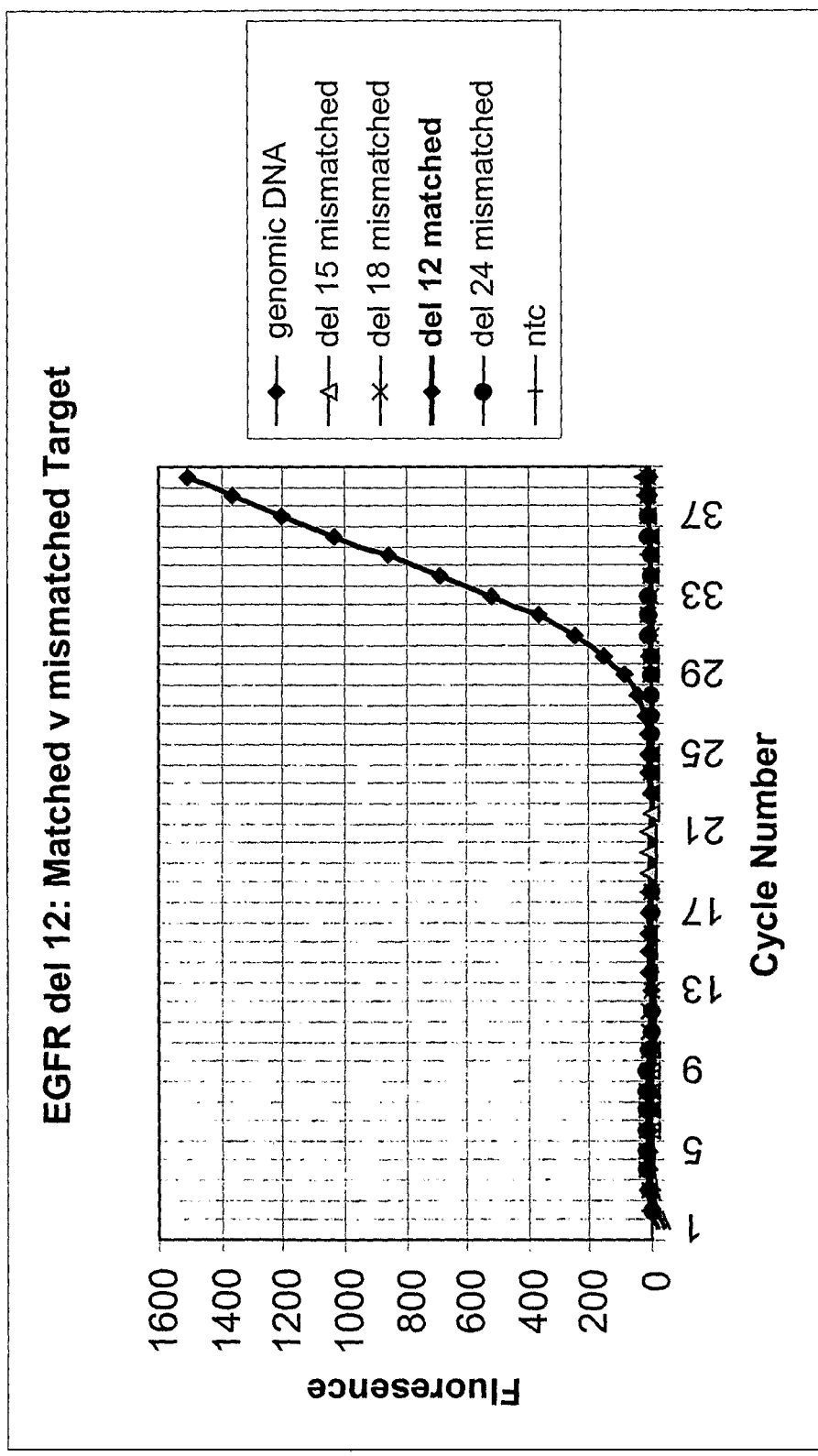
FIG. 1 is a graph showing the results of PCR amplification carried out on a sample in the presence of a primer of the present invention and control primers.

In general terms, the present invention provides a diagnostic method of the detection of EGFR mutations in cancer, which method comprises contacting a test sample of nucleic acid with a diagnostic primer for a EGFR mutation in the presence of appropriate nucleotide triphosphates and an agent for polymerisation, such that the diagnostic primer is efficiently extended only when a EGFR mutation is present in the sample; and detecting the presence or absence of a EGFR mutation by reference to the presence or absence of a diagnostic primer extension product.

There are disclosed herein, primers (SEQ. ID NOS: 1 to 9, 21, 22 and 75) which can be used in the method of the invention.

Each of the diagnostic primers detects the presence or absence of one of the following EGFR mutations:
1) del E746-A750 (two different mutations exist)
2) del L747-T751 insS
3) del L747-P753 insS
4) del S752-I759
5) Exon 21 L858R,
6) Exon 21 L861Q,
7) Exon 18 G719C
8) Exon 18 G719S
9) Exon 20 T790M Mutations 1) to 8) confer sensitivity of an individual to gefinitib whereas mutation 9) confers resistance to gefinitib.

In some embodiments, diagnostic primers specific for the corresponding mutations on the opposite DNA strand are used (SEQ. ID NOS: 25 to 34).

The test sample of nucleic acid is conveniently a sample of blood, faeces, sputum, colonic lavage, bronchial lavage or other body fluid, or tissue obtained from an individual. The individual is conveniently human, preferably Homo sapiens. It will be appreciated that the test sample may equally be a nucleic acid sequence corresponding to the sequence in the test sample. That is to say that all or a part of the region in the sample nucleic acid may firstly be amplified using any convenient technique such as PCR or whole genome amplification (WGA) before use in the method of the invention.

Any convenient enzyme for polymerisation may be used provided that it does not affect the ability of the DNA polymerase to discriminate between normal and mutant template sequences to any significant extent. Examples of convenient enzymes include thermostable enzymes which have no significant 3'-5' exonuclease activity, for example Taq DNA polymerase, particularly "Ampli Taq Gold"™ DNA polymerase (PE Applied Biosystems), Stoffel fragment, or other appropriately N-terminal deleted modifications of Taq or Tth (*Thermus thermophilus*) DNA polymerases.

There are disclosed herein primers for the above EGFR point mutations which have been shown to detect the specific mutations reliably and robustly. Therefore in a further aspect of the invention we provide diagnostic primers comprising SEQ. ID NOS: 1 to 9, 21, 22, 25 to 34 or 75 and derivatives thereof wherein 6-8 of the nucleotides at the 3' end are identical to the sequences and wherein up to 10, such as up to 8, 6, 4, 2, 1, of the remaining nucleotides are optionally varied without significantly affecting the properties of the diagnostic primer. Conveniently, the sequence of the diagnostic primer is exactly as shown in any one of SEQ. ID NOS: 1 to 9, 21, 22, 25 to 34 or 75.

It is to be appreciated that alternative versions of the above described diagnostic methods are configured so that extension of the diagnostic primer indicates the absence of the EGFR mutation. For example, in the embodiments the primers comprise 6-8 nucleotides from the 3' end of any one of SEQ. ID NOS. 10 to 14, 23 or 74. In some embodiments, primers specific for the wild type sequences present the corresponding section of the complementary DNA strand are used (SEQ. ID NOS. 35 to 40).

In many embodiments, it is convenient to use a diagnostic primer of the invention with a further amplification primer in one or more cycles of PCR amplification. A convenient example of this aspect is set out European patent number EP-A-1-0332435. The further amplification primer is either a forward or a reverse common primer. Examples of such common primers are SEQ. ID NOS: 15 to 18, 24 and 76 and, to be used in conjunction with the primers for the complementary strand, SEQ. ID NOS: 41 to 45.

Any convenient control primer pair may be used. Control primers from an unrelated region of the genome, namely part of the human albumen gene, are used herein.

The diagnostic methods of the invention as outlined above are conveniently effected in one or more reaction vessels in some embodiments. Where more than one diagnostic mutation is to be assayed, the diagnostic primer (and corresponding amplification primer) are provided in individual tubes i.e. one tube per mutation in certain embodiments. Alternatively, the reactions are multiplexed, that is to say that all the diagnostic primers and amplification primers are in one tube (see EP-A-1-0332435) in other embodiments.

A variety of methods may be used to detect the presence or absence of diagnostic primer extension products and/or amplification products. These will be apparent to the person skilled in the art of nucleic aid detection procedures. Preferred methods avoid the need for radio-labelled reagents. Particular detection methods include "TaqMan"™ product detection, for example as described in U.S. Pat. No. 5,487,972 & U.S. Pat. No. 5,210,015; Scorpions (WO-A-99/066071), which has particular benefits because specific diagnostic primers may be linked to a specific detector fluorophore, allowing the detection of multiple mutation targets from the same region of the genome.

Conveniently, real-time detection is employed which allows the quantitation of the mutation(s) within the sample. More specifically, the number of cycles required to amplify a DNA sample to a predetermined level using primers specific for the wild-type sequences is compared with the number of cycles required using primers specific for a mutant sequence. By the use of this comparison and by reference to control amplifications containing standardised proportions of mutant target, the ratio of the amount of DNA in the sample containing the mutation relative to the amount of wild type DNA is quantified. Of course this only relates to the sample as presented and does not compensate for low tumour representation within the sample. For this reason, it is preferred to combine this quantitative allele specific approach with a method to estimate the level of tumour within the sample. Alternatively, the quantitative allele specific approach is combined with a method to enrich the sample by specifically excising the tumour material from the overall sample.

In some embodiments, one or more of the diagnostic primers of the invention is conveniently packaged with instructions for use in the method of the invention and appropriate packaging and sold as a kit. The kits conveniently include one or more of the following: appropriate nucleotide triphosphates, for example dATP, dCTP, dGTP, dTTP, a suitable polymerase as previously described, and a buffer solution.

The invention will now be illustrated but not limited by reference to the following Examples.

Materials And Methods

Construction of Synthetic Templates

In the absence of validated and uniform genomic material that carries each of the mutations, it was necessary to construct synthetic templates. For EGFR deletion tests this was done using long synthetic overlapping oligonucleotides, each comprising approximately half the desired amplicon. The sequences of these long oligonucleotides are shown in Table 1.

TABLE 1

| Name | Sequence | SEQ. ID NO. |
|---|---|---|
| EGFRDEL 15 CONFOR | AAAATTCCCGTCGCTATCAAAACATCTCCGAA AGCCAACAAGGAAATCCTCGATGTGAGTTTCT GCTTTGCTGTGTGGGGGTCCATGGCTCTGAAC CTCA | 47 |
| EGFRDEL 15 CONREV | AACATTTAGGATGTGGAGATGAGCAGGGTCTA GAGCAGAGCAGCTGCCAGACATGAGAAAAGGT GGGCCTGAGGTTCAGAGCCATGGACC | 48 |
| EGFRDEL 18 CONFOR | CGCTATCAAGGAATCGAAAGCCAACAAGGAAA TCCTCGATGTGAGTTTCTGCTTTGCTGTGTGG GGGTCCATGGCTCTGAACCTCAGGCCCACCTT TTCT | 49 |
| EGFRDEL 18 CONREV | AGAAAGACATAGAAAGTGAACATTTAGGATGT GGAGATGAGCAGGGTCTAGAGCAGAGCAGCTG CCAGACATGAGAAAAGGTGGGCCTGAGGT | 50 |
| EGFRDEL 24 CONFOR | GCTATCAAGGAATTAAGAGAAGCAACACTCGA TGTGAGTTTCTGCTTTGCTGTGTGGGGGTCCA TGGCTCTGAACCTCAGGCCCACCTTTTCTCAT GTCT | 51 |
| EGFRDEL 24 CONREV | AGAAAGACATAGAAAGTGAACATTTAGGATGT GGAGATGAGCAGGGTCTAGAGCAGAGCAGCTG CCAGACATGAGAAAAGGTGGGC | 52 |
| EGFRDEL 12 CONFOR | AATTCCCGTCGCTATCAAGGAACCATCTCCGA AAGCCAACAAGGAAATCCTCGATGTGAGTTTC TGCTTTGCTGTGTGGGGGTCCATGGCTCTGAA CCTC | 53 |
| EGFRDEL 12 CONREV | GTGAACATTTAGGATGTGGAGATGAGCAGGGT CTAGAGCAGAGCAGCTGCCAGACATGAGAAAA GGTGGGCCTGAGGTTCAGAGCCATGGACC | 54 |

In order to construct the targets, the two overlapping ½-amplicons were mixed in equimolar concentrations in the presence of polymerase, buffer and dNTPs. The primer mix was then incubated for 25 cycles of 1 minute each with an increment of 1° C. per cycle from 50° C. to 75° C. Synthetic templates were subsequently diluted 1 in 1 million into genomic DNA for use as controls in PCR reactions.

For SNP tests synthetic cassettes were produced using PCR to incorporate required mutations into two half cassettes. Half cassettes were then mixed in equimolar concentrations and used as a template for the construction of full length cassettes containing the required SNP target mutation. Specific primer sequences for the construction of cassettes are shown in Table 2.

TABLE 2

| Name | Sequence | SEQ. ID NO. |
|---|---|---|
| EGFR Ex18 AU | CGCCATGCACAACTTCCCTAC | 55 |
| EGFR Ex18 AL | TCCAGAATTTAATGATGCTGCGTCT | 56 |
| EGER Ex18 ML | GAACGCACCGGAGCACA | 57 |
| EGFR Ex18 BU | TTGGTGACATGTTGGTACATCCATC | 58 |
| EGFR Ex18 MU | TTCAAAAAGATCAAAGTGCTGTGC | 59 |

TABLE 2-continued

| Name | Sequence | SEQ. ID NO. |
|---|---|---|
| EGER Ex18 BL | CGTTAACTGGCAATTGTGAGATGGT | 60 |
| EGFR Ex21 AU | AGTCCAGTAAGTTCAAGCCCAGGTC | 61 |
| EGFR Ex21 AL | GTTCCTTAGGTGTCCTTGACAGCAG | 62 |
| EGFR Ex21 L858R ML | CCAGCAGTTTGGCCCGC | 63 |
| EGFR Ex21 BU | CAGAGATTTCAATTGCAGCGAGATT | 64 |
| EGFR Ex21 L858R MU | AGATCACAGATTTTGGGCGGG | 65 |
| EGFR Ex21 BL | TAGGTTTCTGAGCACCCTCTGTGTC | 66 |
| EGFR Ex21 L861Q ML | TCTCTTCCGCACCCAGCTGT | 67 |
| EGFR Ex21 L861Q MU | TTGGGCTGGCCAAACAGC | 68 |
| EGFR Ex20 T790M MU | ACCGTGCAGCTCATCATGC | 46 |
| EGFR Ex20 T790M BL | GCTGTGAAATACCTGGCTTGTTGTT | 69 |
| EGFR Ex20 T790M BU | GAAGGGCATGAGCTGCATG | 70 |
| EGFR Ex20 T790M ML | CCAGGCAGCCTTTAGTCACTGTAGA | 71 |
| EGFR Ex20 T790M AU | GGCCTCTCTGTCATGGGGAAT | 72 |
| EGFR Ex20 T790M AL | ACCTGCTCCACTCCACCACTATCAC | 73 |

Variant Specific PCR

Specific primer sequences for each ARMS reaction and control are shown in Tables 3 and 4.

Reactions were performed in 0.2 ml vessels (single tubes, strips or plates). Reactions (25 μl) typically contained:

250 nM diagnostic primer 250 nM reverse primer 250 nM each of control primers (where used)

200 μM each dNTP 10 mM Tris-HCl (pH 8.3)

50 mM KCl 2.5-4 mM MgCl2

Some reactions performed better in the presence of Qiagen Multiplex Reaction buffer that contains a proprietary mixture of Ammonium Sulphate, $MgCl_2$, and volume excluders such as Poly (ethylene glycol) MW 8000, and/or Dextran (MW 50,000); see US-A-2004-0115712.

For Real Time Quantitative PCR, YO-PRO-1 (Molecular Probes) was included at a final concentration of 1 μM. This dye binds double-stranded DNA and fluoresces with high efficiency, enabling a general detection of PCR product in a reaction. Alternatively, and more preferred, we used Scorpions (a molecule that combines a primer and fluorogenic probe), which offers specific detection of target amplicons.

TABLE 3

Allele Specific primers (1)

| Test | WILD TYPE PRIMERS | | | MUTANT PRIMERS | | | COMMON PRIMERS | | |
|---|---|---|---|---|---|---|---|---|---|
| | NAME | SEQ ID NO. | SEQUENCE | NAME | SEQ ID NO. | SEQUENCE | NAME | SEQ ID NO. | SEQUENCE |
| del L747-T751 insS | EGFR WTA | 10 | CGT CGC TAT CAA GGA ATT AAG AGA AGC | EGFR DEL 12 | 1 | CCC GTC GCT ATC AAG GA CCA | EGFR EX19 REV | 15 | GAG ATG AGC AGG GTC TAG AGC AGA G |
| del E746-A750 | EGFR WTA | 10 | CGT CGC TAT CAA GGA ATT AAG AGA AGC | EGFR DEL 15 | 2 | TTA AAA TTC CCG TCG CTA TCA AAA C | EGFR EX19 REV | 15 | GAG ATG AGC AGG GTC TAG AGC AGA G |
| del E746-A750 Scorpions | EGFR WTA Scorpion | 19 and 10 | FAM CCGCGG GATTTCCTTG TGGCTTTCG CCGCGG BHQ1 HEG CGTCGCTATCA AGGAATTAAGA GAAGC | EGFR DEL 15 Scorpions | 19 and 3 | CAL RED CCG CGG GATTTCC TTGTTGGCTT TCG CCGCGG BHQ2 HEG TTAAAATTCCC GTCGCTATCAA AAC | EGFR EX19 REV | 15 | GAG ATG AGC AGG GTC TAG AGC AGA G |
| del L747-P753 insS | EGFR WT | 11 | GAG AG CA CAT CTC CGA AAG CC | EGFR DEL 18 | 4 | CCG TCG CTA TCA AGG AAT CGA | EGFR EX19 REV | 15 | GAG ATG AGC AGG GTC TAG AGC AGA G |
| del S752-I759 | EGFR WT | 11 | GAG AG CA CAT CTC CGA AAG CC | EGFR DEL 24 | 5 | CAA GGA ATT AAG AGA AGC AAC ACT CGA | EGFR EX19 REV | 15 | GAG ATG AGC AGG GTC TAG AGC AGA G |
| Exon 21 L858R | EGFR EX21 L858R WT | 12 | CAT GTC AAG ATC ACA GAT TTT GGC CT | EGFR EX21 L858R MUT | 6 | CAT GTC AAG ATC ACA GAT TTT GGG AG | EGFR EX21 L858R COM | 16 | GCT GAC CTA AAG CCA CCT CCT TAC T |
| Exon 21 L858R Scorpions | EGFR EX21 L858R WT Scorpion | 20 and 12 | FAM CCGCGG ATTCTTTCTCT TCCGCACCCCC GCGG BHQ1 HEG CATGTCA AGATCACAGAT TTTGGCCT | EGFR EX21 L858R MUT Scorpions | 20 and 6 | CAL RED CCG CGG ATTCTTT CTCTTCCGCA CCC CCGCGG BHQ2 HEG CA TGTCAAGATCA CAGATTTTGGG AG | EGFR EX21 L858R COM | 16 | GCT GAC CTA AAG CCA CCT CCT TAC T |
| Exon 21 L861Q | EGFR EX21 L861Q WT | 13 | TTT CTC TTC CGC ACC CAC CA | EGFR EX21 L861Q MUT | 7 | TTT CTC TTC CGC ACC CAG AT | EGFR EX21 L861Q COM | 17 | CTG TTT CAG GGC ATG AAC TAC TTG G |
| Exon 18 G719C | EGFR EX18 G719C WT | 14 | CTG AAT TCA AAA AGA TCA AAG TGC TCG | EGFR EX18 G719C MUT | 8 | CTG AAT TCA AAA AGA TCA AAG TGC CGT | EGFR EX18 COM | 18 | CCT TTG GTC TGT GAA TTG GTC TCA C |

TABLE 4

Allele Specific primers (2)

| Test | WILD TYPE PRIMERS | | | MUTANT PRIMERS | | | COMMON PRIMERS | | |
|---|---|---|---|---|---|---|---|---|---|
| | NAME | SEQ ID NO. | SEQUENCE | NAME | SEQ ID NO. | SEQUENCE | NAME | SEQ ID NO. | SEQUENCE |
| Exon 18 G719S | EGFR EX18 G719S WT | 14 | CTG AAT TCA AAA AGA TCA AAG TGC TCG | EGFR EX18 G719S MUT | 9 | CTG AAT TCA AAA AGA TCA AAG TGC CGA | EGFR EX18 COM | 18 | CCT TTG GTC TGT GAA TTG GTC TCA C |
| EGFR del 15 2 | EGFR WTA | 10 | CGT CGC TAT CAA GGA ATT AAG AGA AGC | EGFR del 15 2 For | 21 | TTAAAATTCCC GTCGCTATCAA GACA | EGFR EX19 REV | 15 | GAG ATG AGC AGG GTC TAG AGC AGA G |

TABLE 4-continued

Allele Specific primers (2)

| | WILD TYPE PRIMERS | | | MUTANT PRIMERS | | | COMMON PRIMERS | | |
|---|---|---|---|---|---|---|---|---|---|
| Test | NAME | SEQ ID NO. | SEQUENCE | NAME | SEQ ID NO. | SEQUENCE | NAME | SEQ ID NO. | SEQUENCE |
| EGFR T790M | EGFR T790M FC | 23 | ACCTCCACCGT GCAGCTCATA AC | EGFR T790M FT | 22 | ACCTCCACCGT GCAGCTCATC CT | EGFR T790M Reverse | 24 | ATGGCAAACTC TTGCTATCCCA GGA |
| EGFR T790M | T790M A | 74 | TCCACCGTGCA GCTCATCTC | T790M B | 75 | TCCACCGTGCA GCTCATCTT | EGFR T790M Reverse II | 76 | TTGTCTTTGTG TTCCCGGACAT |
| EGFR T790M | T790M A | 74 | TCCACCGTGCA GCTCATCTC | T790M B | 75 | TCCACCGTGCA GCTCATCTT | EGRR T790M Reverse II Scorpions | 76 and 77 | FAM-CCGGGC TCATGCCCTTC GGCTCCGCGG- DABCYL-HEG- TTGTCTTTGTG TTCCCGGAC AT-3' |

PCRs were performed in Real Time PCR cyclers (Mx4000 and Mx3000P from Stratagene), using standard conditions:

95° C. for 10-15 minutes to activate the hot-start enzyme, followed by up to 50 cycles of:

95° C., 60 s

65° C., 60 s—Deletion tests

For SNP tests, the anneal/extend step was modified to 60° C., for 60 s.

Measurement of Extracted DNA

The amount of DNA extracted from each tumour sample was measured by real time amplification of a control locus. Standard curves for this reaction were generated using known concentrations of high quality DNA extracted from cell lines (ECACC, Wiltshire, UK).

Sequencing of Controls and Positive Samples

Sequencing was performed on amplicons generated from exon specific primers, by standard cycle sequencing, using big dye terminators. Reactions were separated using an ABI 3100 capillary sequencing instrument, according to the manufacturer's instructions.

Results and Discussion

ARMS Tests Development and Validation

ARMS tests specific for each of the deletions and SNPs were tested against:

1. "normal" genomic DNA (gDNA)
2. mismatched synthetic targets
3. synthetic target diluted in buffer
4. synthetic target diluted in gDNA (to mimic the tumour situation)
5. No template (water instead of template)

Reactions included the fluorescent DNA binding dye YO-PRO-1 and were monitored in real time. In such reactions, the point at which amplification becomes visible above baseline (known as the Ct) is an indicator of the quantity of target.

Primers which are specific for the same mutations but on the complementary DNA strand have also been developed and these are shown in Tables 5 and 6.

TABLE 5

Allele Specific primers for Reverse Strand (I)

| | WILD TYPE PRIMERS | | | MUTANT PRIMERS | | | COMMON PRIMERS | | |
|---|---|---|---|---|---|---|---|---|---|
| Test | NAME | SEQ ID NO. | SEQUENCE | NAME | SEQ ID NO. | SEQUENCE | NAME | SEQ ID NO. | SEQUENCE |
| del L747-T751 insS | EGRF WT Rev del 15 + 12 | 35 | GGCTTTCGGAGA TGTTGCTTCTC | EGFR del 12 rev | 25 | CTTGTTGGCTTT CGGAGATGGT | EGFR Ex 19 For | 41 | CTGGTAACATC CACCCAGATCA CTG |
| del E746-A750 | EGFR WT Rev del 15 + 12 | 35 | GGCTTTCGGAGA TGTTGCTTCTC | EGFR del 15 1 rev | 26 | TTGTTGGCTTTC GGAGATGTTTTG | EGFR Ex 19 For | 41 | CTGGTAACATC CACCCAGATCA CTG |
| deL L747-P753 insS | EGFR WT Rev 18 + 24 | 36 | GCTTCTCTTAAT TCCTTGATAGCG ACG | EGFR del 18 rev | 27 | GGATTTCCTTGT TGGCTTTCGAT | EGFR Ex 19 For | 41 | CTGGTAACATC CACCCAGATCA CTG |

TABLE 5-continued

Allele Specific primers for Reverse Strand (I)

| Test | WILD TYPE PRIMERS | | | MUTANT PRIMERS | | | COMMON PRIMERS | | |
|---|---|---|---|---|---|---|---|---|---|
| | NAME | SEQ ID NO. | SEQUENCE | NAME | SEQ ID NO. | SEQUENCE | NAME | SEQ ID NO. | SEQUENCE |
| deL S752-I759 | EGFR WT Rev 18 + 24 | 36 | GCTTCTCTTAAT TCCTTGATAGCG ACG | EGFR del 24 Rev | 28 | CAAAGCAGAAAC TCACATCGAGTG | EGFR Ex 19 For | 41 | CTGGTAACATC CACCCAGATCA CTG |
| Exon 21 L858R | EGFR L858R RT | 37 | CTCTTCCGCACC CAGCAGTTTGGT CA | EGFR L858R RG | 29 | CTCTTCCGCACC CAGCAGTTTGGC AC | EGFR L858R Forward | 42 | TTCCCATGATG ATCTGTCCCTC ACAGCA |
| Exon 21 L861Q | EGFR L861Q FA | 38 | ATCACAGATTTT GGGCTGGCCAAT CA | EGFR L861Q FT | 30 | ATCACAGATTTT GGGCTGGCCAAT AA | EGFR L861Q Reverse | 43 | GAGCTCACCCA GAATGTCTGGA GAGCAT |
| Exon 18 G719C | EGFR G719 R WT | 39 | TATACACCGTGC CGAACGCACCGG AGAC | EGFR G719C RT | 31 | TATACACCGTGC CGAACGCACCGG AACA | G719 Forward | 44 | GGGCTGAGGTG ACCCTTGTCTC TGTGTT |
| Exon 18 G719S | EGFR G719 R WT | 39 | TATACACCGTGC CGAACGCACCGG AGAC | EGFR G719S RA | 32 | TATACACCGTGC CGAACGCACCGG ATCT | G719 Forward | 44 | GGGCTGAGGTG ACCCTTGTCTC TGTGTT |
| EGFR del 15 2 Reverse | EGFR WT Rev del 15 + 12 | 35 | GGCTTTCGGAGA TGTTGCTTCTC | EGFR del 15 2 rev | 33 | TTGTTGGCTTTC GGAGATGTCT | EGFR Ex 19 For | 41 | CTGGTAACATC CACCCAGATCA CTG |

TABLE 6

Allele Specific primers for Reverse Strand (II)

| Test | WILD TYPE PRIMERS | | | MUTANT PRIMERS | | | COMMON PRIMERS | | |
|---|---|---|---|---|---|---|---|---|---|
| | NAME | SEQ ID NO. | SEQUENCE | NAME | SEQ ID NO. | SEQUENCE | NAME | SEQ ID NO. | SEQUENCE |
| EGFR T790M Reverse | EGFR T790M RT WT | 40 | AGCCGAAGGGC ATGAGCTTCA | EGFR T790M | 34 | AGCCGAAGGG CATGAGCTG AG | EGFR T790M Forward | 45 | GCACAGCTTT TCCTCCATGA GTACG |

Example 1

The mutation specific primer EGFR Del 12 was tested against matched synthetic target and three mismatched mutant synthetic targets (del 15 (1), del 18 and del 24), as well as normal DNA and a water control. The results are shown in FIG. 1.

It is clear that in this reaction the primer shows absolute specificity for its own target and does not detect wild type sequences nor any of the other deletion mutations found in the same genomic region.

Example 2

Use of ARMS Tests on Tumour Samples

Forty-two DNA samples from Non-Small Cell Lung Cancers and cell lines were analysed using each of the mutation specific primers SEQ. ID NOS: 1 to 9. Tumour DNA had been extracted from paraffin embedded tissue on slides.

A number of samples were found to be positive using this method: nine for the L858R SNP and one for the 15 base pair deletion del E746-A750.

Confirmatory sequencing was performed for the region surrounding the putative mutations.

Figure 2:
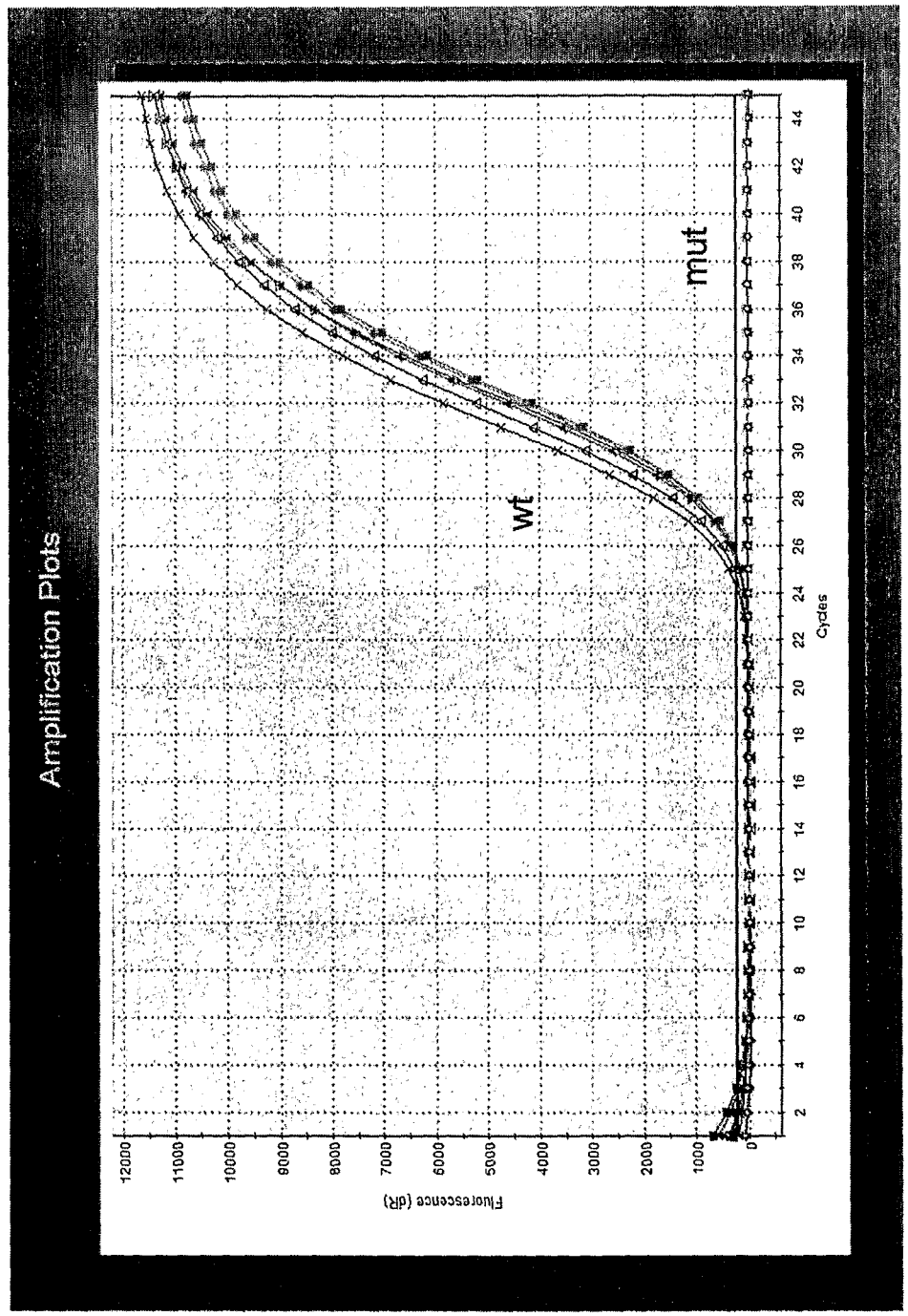
FIG. 2 is a graph showing the results of PCR amplification carried out on a sample in the presence of a primer specific for del S752-I759 (SEQ. ID NO. 5) and a corresponding wild-type specific primer.

FIG. 2 shows a typical negative result for a batch of 8 samples tested with the del S752-I759 specific primers. It is clear that the wild type specific reactions perform efficiently while the mutation specific primers (SEQ. ID NO: 5) do not amplify indicating the absence of this mutation in these samples.

Figure 3:
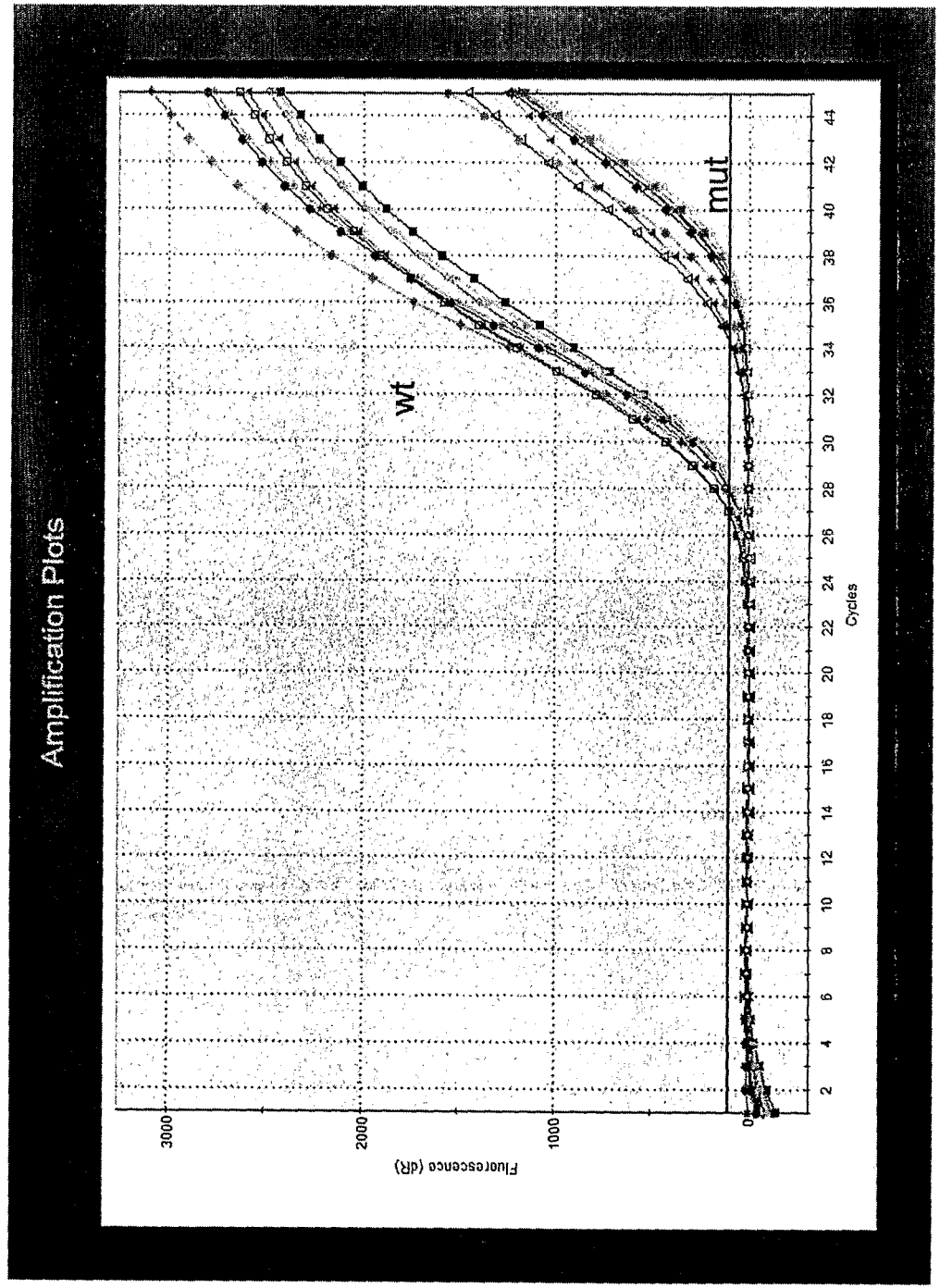
FIG. 3 is a graph showing the results of PCR amplification carried out on a sample in the presence of a primer specific for the L858R mutation (SEQ. ID NO. 6) and a corresponding wild-type specific primer.

FIG. 3 shows the L858R analysis for 8 positive samples. In each case, the reaction using the mutation primers (SEQ. ID NO: 6) is positive as is the wild type reaction. The fact that the mutant reaction appears several cycles later than the corresponding wild type reaction indicates that the mutation is not the majority sequence in the samples.

Figure 4:
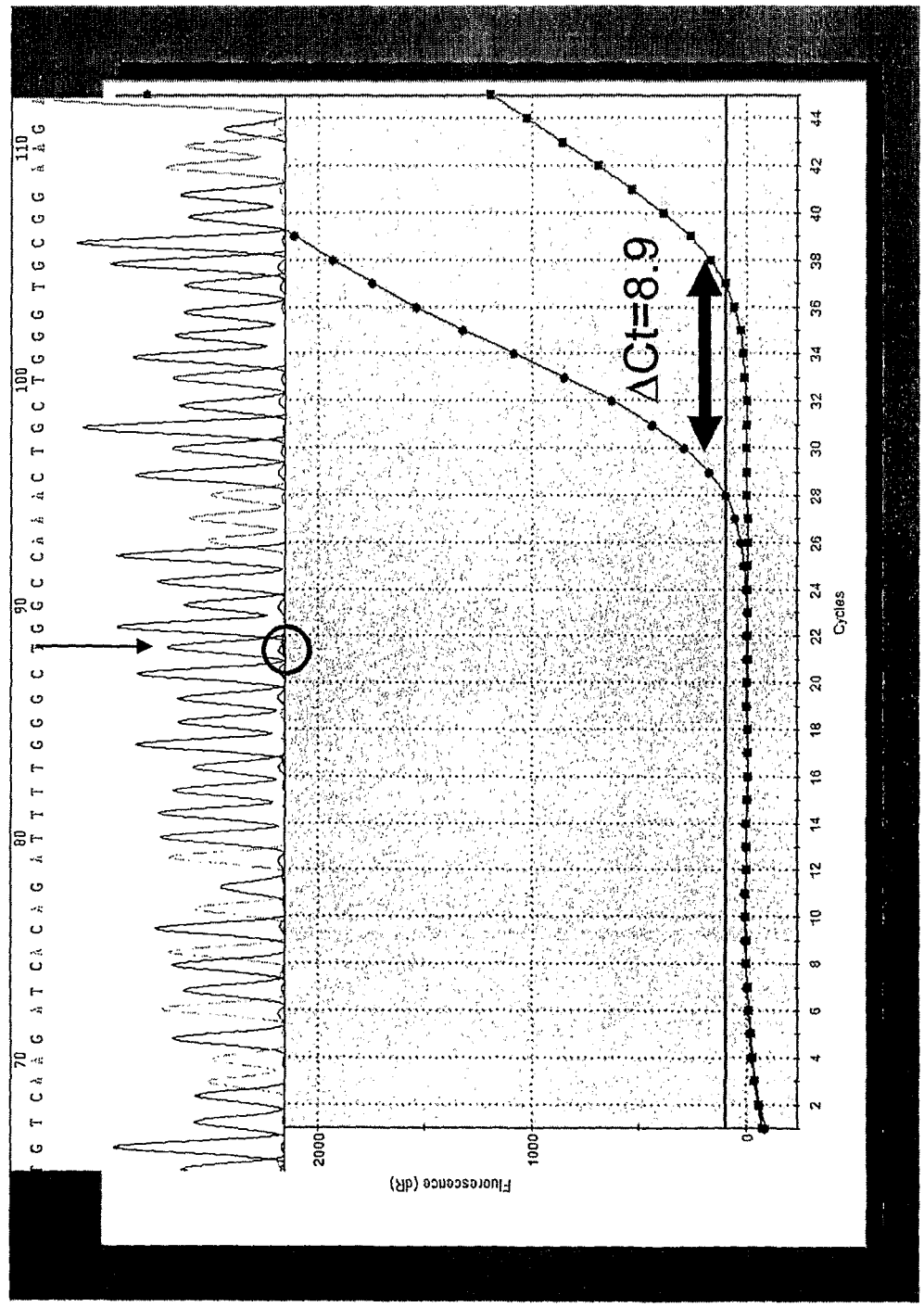
FIG. 4 is a graph (lower) showing the results of PCR amplification carried out on a sample in the presence of a primer specific to a mutation and a corresponding wild-type specific primer, and a graph (upper) showing the results of sequencing of the sample.

FIG. 4 shows more detailed analysis of the allele specific PCR analysis, combined with sequencing of the same exon from this sample. In this sample, the sequencing approach would have failed to detect the mutation that was clearly identified by the ARMS approach (no peak is visible at the circled position).

Figure 5:
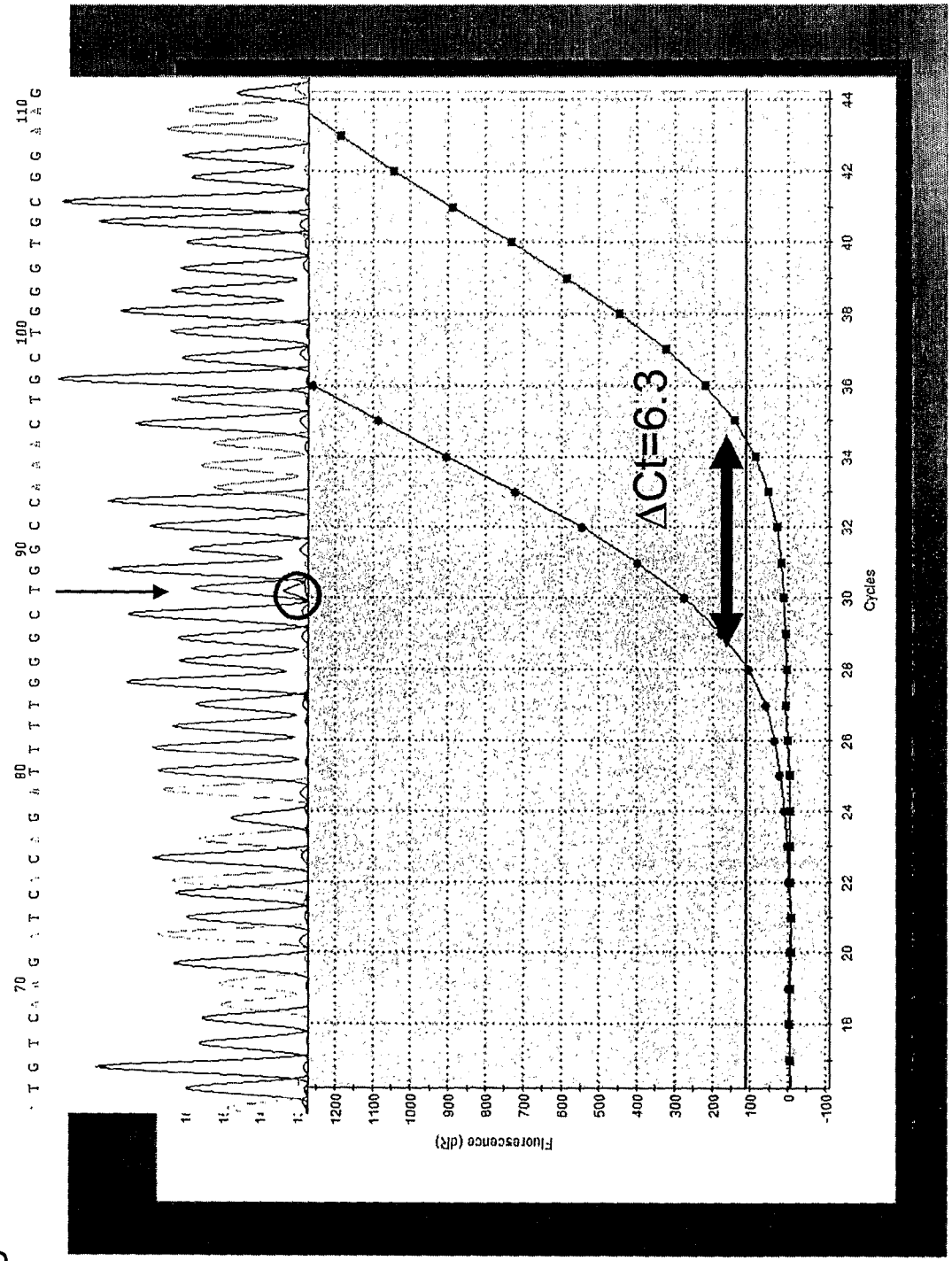
FIG. 5 is a graph (lower) showing the results of PCR amplification carried out on a sample in the presence of a primer specific to a mutation and a corresponding wild-type specific primer, and a graph (upper) showing the results of sequencing of the sample.

FIG. 5 shows more detailed analysis of the allele specific PCR analysis, combined with sequencing of the same exon from this sample. In this sample, the sequencing approach could have detected the mutation that was clearly identified by the ARMS approach (a very weak peak is visible at the circled position). The differential (ΔCt) between the wild type and mutant specific reactions was smaller in this sample, indicating that the mutation was relatively more prevalent than in the sample whose analysis is shown in FIG. 4.

Example 3

Figure 6:
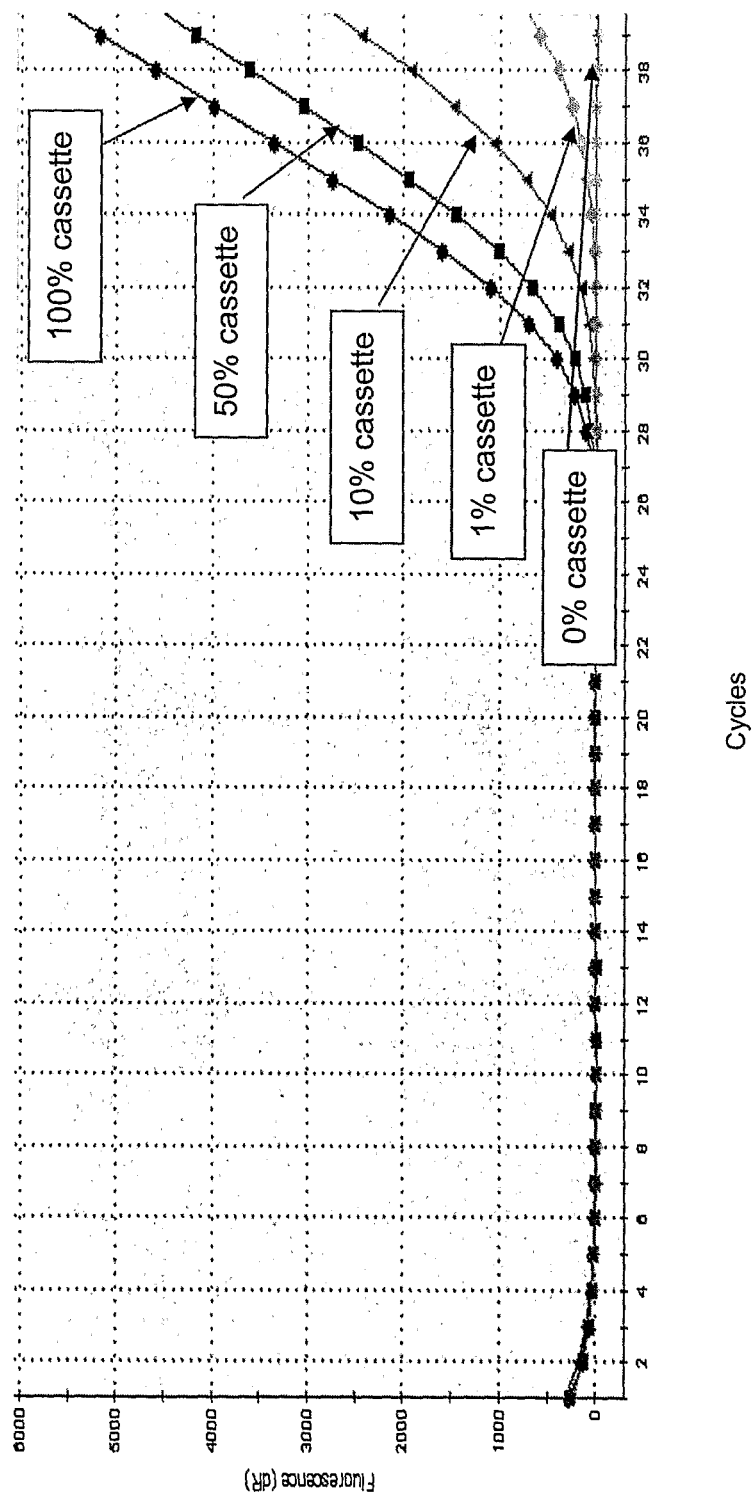
FIG. 6 is a graph showing the results of PCR amplification carried out on a set of samples, in the presence of a primer specific to a mutation.

FIG. 6 shows the results of PCR amplification of samples containing DNA with, and without the T790M mutation. Five DNA samples were provided, each comprising 0%, 1%, 10%, 50% or 100% DNA with the T790M mutation. The samples were amplified using the mutant primer of SEQ. ID NO. 75 and the reverse Scorpion primer of SEQ. ID NOS. 76 and 77.

The results show that the mutant primer was specific for DNA having the T780M mutation because the sample without any DNA having the mutation showed no amplification. Furthermore, detection was shown to be quantitative in that the Ct (threshold cycle) was related directly to the relative amount of matched target, even in the presence of excess unmatched target.

Figure 7:
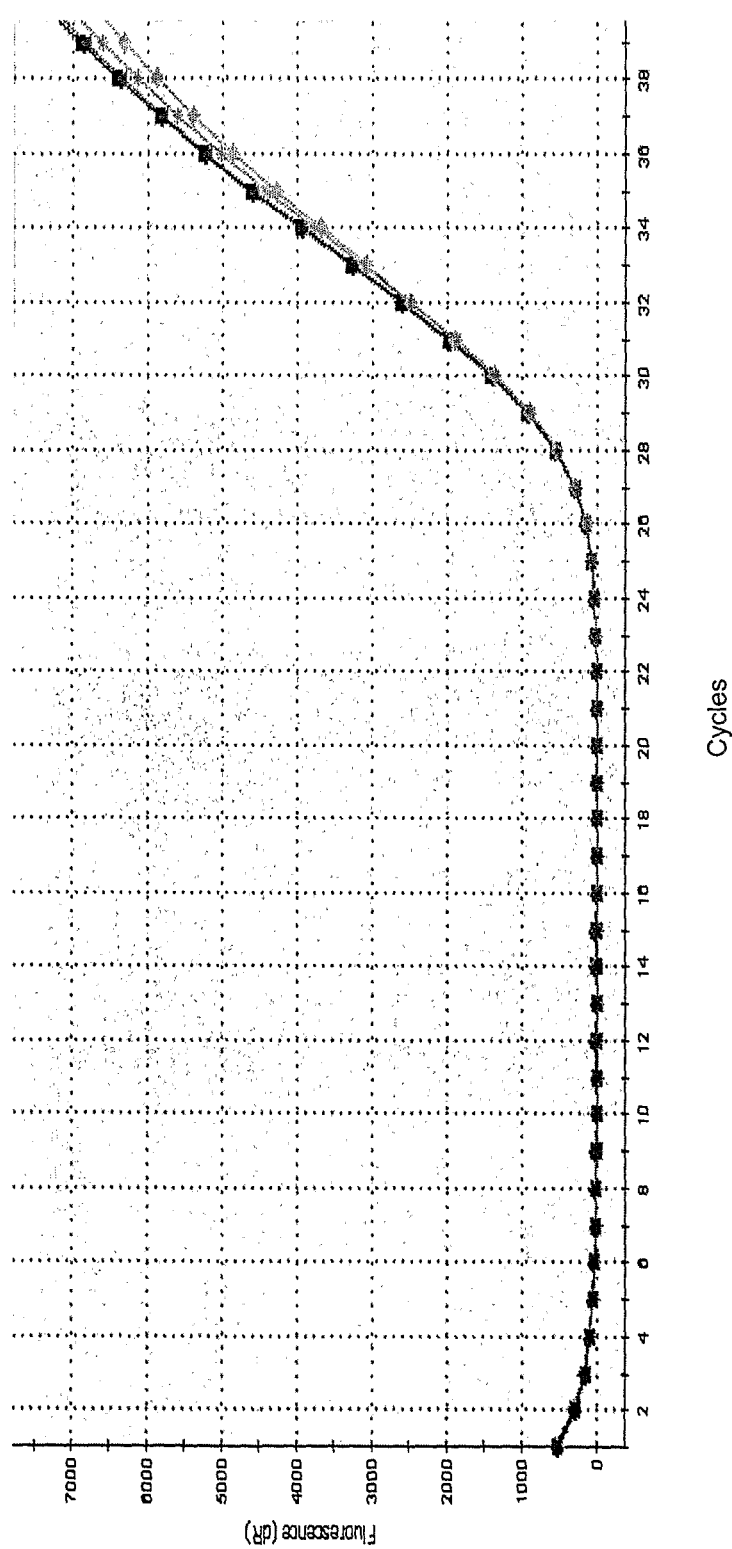
FIG. 7 is a graph showing the results of PCR amplification, using control primers, of the samples analysed in the results shown in FIG. 6.

FIG. 7 shows the results of a control assay carried out on the samples which were tested and reported in FIG. 6. PCR amplification was carried out using control primers. FIG. 7 confirms that each sample had the same total amount of target since the threshold cycles for each sample were the same in this control amplification.

The invention claimed is:

1. An isolated EGFR mutation diagnostic primer comprising one of the following primer sequences, or the sequence complementary to one of the following primer sequences: SEQ. ID NOS. 1, 2, 4, 5, 6, 19, 20, 21 or 75, wherein the primer further comprises a quencher group and a fluorophore group.

2. A primer according to claim 1 wherein the quencher group and the fluorophore group are separated by a nucleotide tail sequence comprising first and second regions, the nucleotides of the first region being complementary to but in reverse order from the nucleotides of the second region, whereby hybridisation of the first region to the second region results in the quencher group to be sufficiently close to the fluorophore group to quench the fluorophore group.

3. A primer according to claim 2 wherein the tail sequence further comprises a third region having a sequence complementary to a region of the EGFR gene.

4. An isolated EGFR mutation diagnostic primer comprising at least the six nucleotides at the 3' end of SEQ. ID NO. 6 further comprising a quencher group and a fluorophore group, wherein the quencher group and the fluorophore group are separated by a tail sequence comprising SEQ. ID NO. 20.

5. A primer according to claim 1 wherein the quencher group comprises black hole quencher 1 (BHQ1) and the fluorophore group comprises FAM.

6. A primer according to claim 1 wherein the quencher group comprises black hole quencher 2 (BHQ2) and the fluorophore comprises Cal Red.

7. A kit comprising at least a pair of polynucleotides for combined use, wherein one member of the pair of polynucleotides is an EGFR mutation diagnostic primer and comprises SEQ ID NO: 75 or the sequence complementary to SEQ ID NO: 75 and the other member of the pair of polynucleotides comprises SEQ ID NO: 76 or the sequence complementary to SEQ ID NO: 76, wherein one of the polynucleotides comprises a fluorophore group.

8. A kit comprising at least a set of three polynucleotides for combined use, wherein the set of three polynucleotides comprises one of the following sets of three primer sequences, respectively, or sequences complementary thereto: SEQ. ID NOS. 1, 10 and 15, or SEQ. ID NOS. 2, 10 and 15, or SEQ. ID NOS. 4, 11 and 15, or SEQ. ID NOS. 5, 11 and 15, or SEQ. ID NOS. 6, 12 and 16, or SEQ. ID NOS. 21, 10 and 15, or SEQ. ID NOS. 74, 75 and 76, wherein one of the polynucleotides of each set comprises a fluorophore group.

9. A kit according to claim 7 further comprising nucleotide triphosphates, a polymerisation enzyme and/or a buffer solution.

10. A method of detecting the presence or absence of a mutation in the EGFR gene comprising the steps of:
   a) mixing a nucleic acid sample comprising at least a fragment of the EGFR gene with an EGFR mutation diagnostic primer, wherein said primer comprises one of the following primer sequences, or the sequence complimentary to one of the following primer sequences: SEQ. ID NOS. 1, 2, 4, 5, 6, 19, 20, 21 or 75; and
   b) detecting hybridisation of the EGFR mutation diagnostic primer to the nucleic acid sample wherein hybridisation indicates the presence or absence of a mutation.

11. A method according to claim 10, wherein step b) comprises carrying out DNA polymerisation using the EGFR mutation diagnostic primer as a first primer and detecting the extension product of polymerisation.

12. A method according to claim 11 wherein step b) comprises the step of mixing the nucleic acid sample and the EGFR mutation diagnostic primer with a second primer which corresponds to a region of the fragment of the EGFR sequence downstream of the region to which the EGFR mutation diagnostic primer is complementary and carrying out PCR on the mixture.

13. A method according to claim 12 wherein the second primer comprises: SEQ. ID NO. 15 and the EGFR mutation diagnostic primer comprises SEQ. ID NOS. 1, 2, 4, 5, or 21; SEQ. ID NO. 16 and the EGFR mutation diagnostic primer comprises SEQ. ID NO. 6; or SEQ. ID NO. 76 and the polynucleotide comprises at least four or five of the final six nucleotides of SEQ. ID NO. 75.

14. A method according to claim 11 wherein step a) comprises the step of mixing the nucleic acid sample with a pair of a mutation specific primer and a wild-type specific primer, the pair being selected from: SEQ. ID NO: 1 and SEQ. ID NO: 10; SEQ. ID NO: 2 and SEQ. ID NO: 10; SEQ. ID NO: 4 and SEQ. ID NO: 11; SEQ. ID NO: 5 and SEQ. ID NO: 11; SEQ. ID NO: 6 and SEQ. ID NO: 12; SEQ. ID NO: 21 and SEQ. ID NO: 10; or SEQ. ID NO. 74 and SEQ. ID NO. 75.

15. A method according to claim 14 wherein the nucleic acid sample comprises wild-type sequences and mutated sequences and further comprising step c) wherein the number of amplification cycles required to amplify the wild-type sequences to a predetermined quantity is compared with the number of amplification cycles required to amplify the mutated sequences to the predetermined quantity thereby providing an indication of the ratio of the wild type sequences to mutated sequences in the sample.

16. A method according to claim 15 wherein the nucleic acid sample comprises a portion of tumourous tissue and a portion of non-tumourous tissue and wherein step c) further comprises the step of determining the ratio of tumourous tissue to non-tumourous tissue in the sample.

17. A method according to claim 15 or 16 further comprising the step of, prior to step a), enriching the nucleic acid sample to increase the ratio of tumourous tissue to non-tumourous tissue in the sample.

18. A method according to claim 13 wherein step b) comprises detecting if amplification of at least a portion of the EGFR gene occurs.

19. A method according to claim 10 wherein the EGFR mutation diagnostic primer comprises a quencher group and a fluorophore group and wherein step b) comprises exposing the mixture to light of a wavelength to which the fluorophore is responsive in the absence of the quencher group and detecting light at the wavelength emitted by the fluorophore group in the absence of the quencher group.

20. A composition comprising an EGFR mutation diagnostic primer according to claim 1, wherein the EGFR mutation diagnostic primer is not bound to a solid substrate.

* * * * *